(12) United States Patent
Reisfeld et al.

(10) Patent No.: US 10,335,420 B2
(45) Date of Patent: *Jul. 2, 2019

(54) NANOPARTICLE-BASED TUMOR-TARGETED DRUG DELIVERY

(71) Applicant: The Scripps Research Institute, La Jolla, CA (US)

(72) Inventors: Ralph A. Reisfeld, La Jolla, CA (US); Rong Xiang, San Diego, CA (US); Yunping Luo, San Diego, CA (US); Debbie Liao, San Diego, CA (US); Ze Liu, Beijing (CN); Tingmei Chen, Chongqing (CN); Si Chen, Little Rock, AR (US); Dan Lu, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/495,474

(22) Filed: Apr. 24, 2017

(65) Prior Publication Data
US 2017/0224838 A1     Aug. 10, 2017

Related U.S. Application Data

(63) Continuation-in-part of application No. 13/820,413, filed as application No. PCT/US2011/050287 on Sep. 2, 2011, now Pat. No. 9,629,922, which is a continuation of application No. 13/224,399, filed on Sep. 2, 2011, now Pat. No. 9,616,137.

(60) Provisional application No. 61/402,686, filed on Sep. 2, 2010.

(51) Int. Cl.

| | |
|---|---|
| A61K 9/127 | (2006.01) |
| A61K 31/58 | (2006.01) |
| A61K 47/28 | (2006.01) |
| A61K 31/704 | (2006.01) |
| B82Y 5/00 | (2011.01) |
| A61K 47/69 | (2017.01) |
| A61K 31/4164 | (2006.01) |

(52) U.S. Cl.
CPC .............. *A61K 31/58* (2013.01); *A61K 9/127* (2013.01); *A61K 9/1271* (2013.01); *A61K 9/1272* (2013.01); *A61K 31/4164* (2013.01); *A61K 31/704* (2013.01); *A61K 47/28* (2013.01); *A61K 47/6911* (2017.08); *A61K 47/6913* (2017.08); *B82Y 5/00* (2013.01)

(58) Field of Classification Search
None
See application file for complete search history.

(56) References Cited

U.S. PATENT DOCUMENTS

| | | | | |
|---|---|---|---|---|
| 5,882,679 | A * | 3/1999 | Needham | A61K 9/1075 424/450 |
| 6,339,069 | B1 * | 1/2002 | Meers | A61K 9/127 424/450 |
| 2006/0135410 | A1 * | 6/2006 | Liu | A61K 47/64 514/1.3 |

OTHER PUBLICATIONS

Marion G. Götz, et al. Aza-peptidyl Michael Acceptors. A New Class of Potent and Selective Inhibitors of Asparaginyl Endopeptidases (Legumains) from Evolutionarily Diverse Pathogens. J. Med. Chem. 2008, 51, 2816-2832. (Year: 2008).*

Maria C. Sandström,*, Emma Johansson, and, and Katarina Edwards. Structure of Mixed Micelles Formed in PEG-Lipid/Lipid Dispersions. Langmuir 2007, 23(8), 4192-4198. (Year: 2007).*

Yong Serk Park, Kazuo Maruyama, and Leaf Huang. Some negatively charged phospholipid derivatives prolong the liposome circulation in vivo. Biochimica et Biophysica Acta, 1108 (1992) 257-260. (Year: 1992).*

* cited by examiner

*Primary Examiner* — Michael P Cohen
(74) *Attorney, Agent, or Firm* — Olson & Cepuritis, Ltd.

(57) ABSTRACT

An aqueous tumor-targeting liposome nanoparticle composition comprises an aqueous dispersion of liposome nanoparticles. The nanoparticles preferably encapsulate an anticancer chemotherapeutic agent, which can be added to a pre-formed liposome composition or can be incorporated in the liposomes during the formation of the liposomes. The liposome nanoparticles comprise a legumain-targeting lipid admixed with one or more other micelle or vesicle-forming lipid materials in the form of nanoparticulate liposomes dispersed in an aqueous carrier. A preferred tumor-targeting liposome nanoparticle composition comprises a legumain-targeting lipid component and polyethylene glycol-conjugated lipid component. The legumain-targeting lipid component comprising a hydrophobic lipid portion covalently attached to a legumain-binding moiety.

17 Claims, 12 Drawing Sheets

Aza-Asn Michael acceptor inhibitor

Aza-Asn-epoxide inhibitor

Aza-Asn halomethylketone inhibitor

FIG. 10A   FIG. 10B

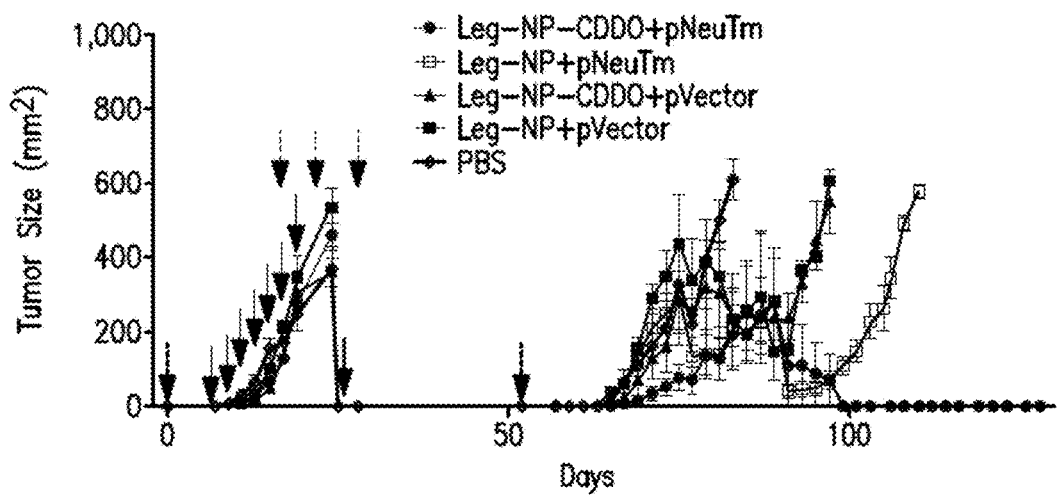
FIG. 11A
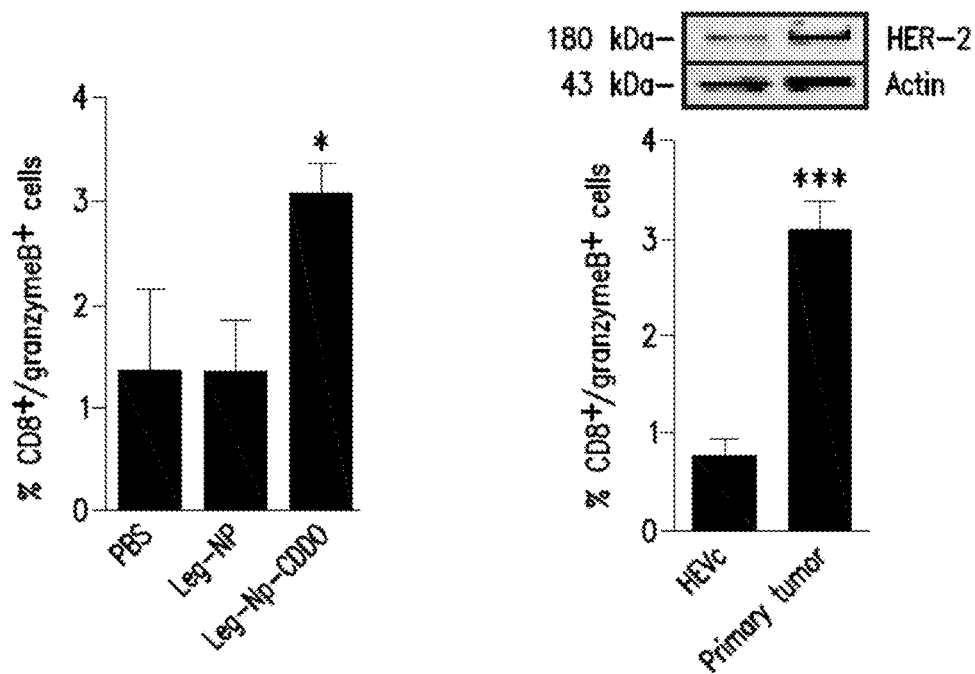
FIG. 11B  FIG. 11C

NANOPARTICLE-BASED TUMOR-TARGETED DRUG DELIVERY

CROSS REFERENCE TO RELATED APPLICATIONS

This application is a continuation-in-part of U.S. patent application Ser. No. 13/820,413, filed on Mar. 1, 2013, now U.S. Pat. No. 9,629,922, which is a 371 of PCT/US2011/050287, filed on Sep. 2, 2011, which is a continuation of and claims the benefit of U.S. patent application Ser. No. 13/224,399, filed on Sep. 2, 2011, now U.S. Pat. No. 9,616,137, and which claims the benefit of U.S. Provisional Patent Application Ser. No. 61/402,686, filed on Sep. 2, 2010, each of which is incorporated herein by reference in its entirety.

GOVERNMENT SUPPORT

This invention was made with governmental support from the United States Government, National Institutes of Health, grant no. 5 R01 CA134364-01A, and National Heart, Lung, and Blood Institute training grant no. T32HL007195.

BACKGROUND

Ligand-targeting has been a major advancement in nanoparticle (NP) mediated drug delivery, achieving high local concentration and low systemic exposure, reducing drug toxicity while maintaining optimal dose delivery to target cells. Proof of concept was established for this strategy with antibodies and homing peptides, which bind adhesion receptors that are over expressed by tumor vasculature, including integrins, and HER-2, and folate cell surface receptors on tumor cells. Concerns associated with ligand-targeting include receptor saturation, low receptor-ligand affinity, limited tissue penetration and genetic heterogeneity of solid tumors. Legumain is an asparaginyl endopeptidase that is overexpressed by a variety of tumor cells. Consequently, legumain provides a convenient target for directing therapeutic agents to tumor cells. The compositions and methods of the present described herein address the concerns associated with ligand-targeting, while providing effective means for tumor-specific drug delivery.

SUMMARY OF THE INVENTION

Tumor-targeted lipid compositions are described herein. The compositions comprise liposome nanoparticles dispersed in an aqueous medium. The liposome nanoparticles are formed from vesicle-forming lipid materials and have a legumain-targeting group covalently attached to the nanoparticles.

In some embodiments described herein an aqueous tumor-targeting liposome nanoparticle composition comprises an aqueous dispersion of liposome nanoparticles that comprise a legumain-targeting lipid component and a polyethylene glycol-conjugated lipid component. The legumain-targeting lipid component comprises a hydrophobic lipid portion covalently attached to a legumain-binding moiety.

In other embodiments an aqueous tumor-targeting liposome nanoparticle composition comprises an aqueous dispersion of liposome nanoparticles optionally encapsulating an anti-cancer chemotherapeutic agent. For example, in some embodiments an aqueous tumor-targeting liposome nanoparticle composition comprises a legumain-targeting lipid admixed with one or more other micelle or vesicle-forming lipid materials in the form of a nanoparticulate liposome dispersion, optionally encapsulating an anti-cancer chemotherapeutic agent within the liposome nanoparticles. The legumain-targeting lipid component comprises a hydrophobic lipid portion covalently attached to a legumain-binding moiety. The anti-cancer chemotherapeutic agent can be encapsulated within the liposome nanoparticles during the preparation of the nanoparticles, or the nanoparticles can be preformed and subsequently loaded with the chemotherapeutic agent.

A preferred aqueous tumor-targeting liposome nanoparticle composition comprises (a) a legumain-targeting lipid component, (b) a zwitterionic lipid component; (c) an amino-substituted lipid component; (d) a neutral lipid component; and (e) a polyethylene glycol-conjugated lipid component dispersed as nanoparticulate liposomes in an aqueous carrier (e.g., a physiologically tolerable buffer, which can include various physiologically acceptable excipients and adjuvants commonly used in drug formulations). The legumain-targeting lipid component comprises a hydrophobic lipid portion covalently attached to a legumain-binding moiety. The legumain-binding moiety can be any material that selectively forms a stable complex or covalent bond with legumain.

A preferred legumain-targeting moiety is an aza-Asn Michael acceptor. A preferred legumain-targeting lipid component comprises an aza-Asn Michael acceptor legumain inhibitor bound to a phospholipid. For example, the legumain-binding active portion of an aza-Asn Michael acceptor known as RR-11a can be bound to a suitable lipid as shown in FIG. 1a.

In some preferred embodiments, the legumain-targeting lipid component comprises legumain-binding moiety covalently attached to a 1,2-diacylglycero-phosphoalkanolamine group, such as 1,2-dioleoyl-sn-gycerol-3-phosphoethanolamine (DOPE).

A preferred zwitterionic lipid component (b) comprises a 1,2-diacylglycero-phosphocholine compound, such as 1,2-di-(9Z-octadecenoyl)-sn-glycero-3-phosphocholine (DOPC).

A preferred amino-substituted lipid component (c) comprises a 1,2-diacylglycero-phosphoalkanolamine compound, such as DOPE.

A preferred neutral lipid component (d) comprises cholesterol.

A preferred polyethylene glycol-conjugated lipid component (e) comprises a polyethylene glycol-conjugated 1,2-diacylglycero-phosphoalkanolamine compound such as 1,2-dioleoyl-sn-gycerol-3-phosphoethanolamine-N-[methoxy (polyethylene glycol] wherein the polyethylene glycol portion of the compound has an average molecular weight of about 2000 atomic mass units (amu).

In one preferred embodiment, the components (a), (b), (c), (d) and (e) are present in the liposome nanoparticles in a molar ratio of (a):(b):(c):(d):(e) of about 1.1:6.7:6.7:2.2:1

Preferably, the liposome nanoparticle composition encapsulates an anti-cancer chemotherapeutic agent, e.g., doxorubicin, 1-[2-cyano-3-,12-dioxooleana-1,9(11)-dien-28-oyl] imidazole (also known as CDDO-Im), or any other known anticancer chemotherapeutic agent The compositions described herein are particularly suited for use in treatment of a legumain-expressing tumor. A method aspect described herein comprises administering to a patient in need of cancer treatment an effective amount of an anti-cancer chemotherapeutic agent encapsulated within the liposome nanoparticles.

BRIEF DESCRIPTION OF THE DRAWINGS

FIG. 1a illustrates conjugation of RR-11a-NHS to 1,2-dioleoyl-sn-glycero-3-phosphoethanolamine (DOPE).

FIG. 1b provides fluorescence microscopy images demonstrating tumor hypoxia (Scale bars, 100 μm).

FIG. 1c provides a graph of specific binding versus antibody concentration demonstrating the affinity of anti-mouse monoclonal antibody (mAb) for cell membrane-expressed legumain, as determined by Scatchard analysis.

FIG. 1d provides a graph of rhodamine-positive cells versus time for murine 4T1 and 4TO7 breast and CT26 colon carcinoma cells cultured for about 24 hours (h) with $CoCl_2$, after which non-targeted nanoparticles (Non-targeted) or RR-11a-targeted nanoparticles (Targeted) NPs were added to the cell (n=3 wells per group; data represent means±s.e.m).

FIG. 1e provides fluorescence microscopy images visualizing distribution of NPs for tumor, liver, spleen and kidney cells from mice treated with targeted (top row) and non-targeted (bottom row) NPs, as indicated by rhodamine B fluorescence (n=2 mice per group; scale bars, 100 μm).

FIG. 2a provides a graph of mean fluorescence intensity (MFI) versus time for 4T1 and 4TO7 cells cultured with $CoCl_2$ for about 24 h and then incubated with a targeted nanoparticle composition loaded with doxorubicin (designated RDZ-218 herein), doxorubicin-loaded non-targeted NPs (NP-Dox), or free doxorubicin (Free Dox) for the indicated times, followed by flow cytometry analysis to determine mean fluorescence intensity (MFI) of doxorubicin (n=3 wells per group for each time point; data represent means±s.e.m).

FIG. 2b provides bar graphs showing the percentage of drug uptake concentration as determined by comparing the MFI of RDZ-218, NP-Dox, and Free Dox-treated cells with that of serially diluted doxorubicin.

FIG. 2c provides a bar graph comparing the relative percentage of dead 4T1 and 4TO7 cells treated with control (no-treatment), Free Dox, NP-Dox, free RR-11a, NP-RR-11a (no doxorubicin), and RDZ-218, approximately 24 h following treatment, as determined by analyzing the forward and side scatter plot of flow cytometry (data is shown relative to untreated cells (Control); n=3 wells per group; data represent means±s.e.m. *p<0.05, **p<0.005).

FIG. 2d provides fluorescence microscopy images of tumor (top row), liver (middle row), and heart (bottom row) cells from female BALB/c mice in which 4TO7 cells were injected into the inguinal mammary fat pad; tumors were allowed to establish for about 5 days (d), to a size of approximately 500 $mm^3$, after which mice were given two i.v. injections with RDZ-218, NP-Dox, or Free Dox; mice were sacrificed about 24 h after the last injection and tissues were isolated and immediately analyzed by fluorescence microscopy to detect distribution of doxorubicin; tissue sections were also stained with DAPI to visualize cell nuclei (n=2 mice per group; scale bars, 100 μm).

FIG. 3a provides a graph of tumor size versus time (data represent means±s.e.m.).

FIG. 3b provides images of primary tumors captured prior to dissection; images are representative from each group.

FIG. 3c provides a bar graph comparing wet tumor weight of primary tumors from mice of each treatment group (data represent means±s.e.m; *p<0.05).

FIG. 3d provides a bar graph comparing TUNEL-positive (apoptotic) tumor cells from mice of each treatment group (n=5 fields per section; data represent means±s.e.m; ***p<0.0005).

FIG. 3e provides a bar graph comparing the change in body weight for mice from each treatment group (the primary tumor weight was subtracted from the total body weight at time of sacrifice and compared to body weight prior to tumor cell challenge to determine change in body weight; data represent means±s.e.m; control groups were compared to the RDZ-218 treated group, p=0.0029, *p<0.001).

FIG. 6A shows Western Blot analysis of 4T1 murine breast cancer cells were treated with IL-6 (long/mL) and CDDO-Im at varying concentrations.

FIG. 6B shows Western Blot analysis of 4TO7 murine breast cancer cells treated with IL-6 (10 ng/mL) in combination with free CDDO-Im (Free CDDO), empty targeted NPs (Leg-NP), non-targeted NP-encapsulated CDDO-Im (NP-CDDO) or targeted NP-encapsulated CDDO-Im (Leg-NP-CDDO).

FIG. 6C shows Western Blot analysis of MMTV-Neu primary tumor extracts prepared from mice treated with 8 i.v. injections of PBS (Lane 1), Leg-NP (Lane 2) or Leg-NP-CDDO (Lane 3).

FIG. 7A shows a treatment schematic of mice challenged with 5×10³ 4TO7 tumor cells and treated with Leg-NP-CDDO or controls (PBS, free CDDO, NP-CDDO or Leg-NP) (n=8 mice/group).

FIG. 7B shows data for calculated tumor size (by palpation—tumors palpated every 2 days). Data represent means±s.e.m.

FIG. 7C shows data for tumor weights (measured on day 19) compared to body weights to determine percent tumor burden. Data represent means±s.e.m. *p<0.05.

FIG. 8A shows a treatment schematic of mice challenged with 1×10⁴ MMTV-Neu primary tumor cells and treated with Leg-NP-CDDO or controls (PBS or Leg-NP) (n=8 mice/group).

FIG. 8B shows data for calculated tumor size (by palpation—tumors were palpated every 3 days). Data represent means±s.e.m.

FIG. 8C shows data for tumor weights (measured on day 46) compared to body weights to determine percent tumor burden. Data represent means±s.e.m, *p<0.05.

FIG. 9A shows expression of Th1 from Western blot analysis (left) quantified relative to Actin (right).

FIG. 9B shows expression of Th2 from Western blot analysis (left) quantified relative to Actin (right).

FIG. 9C shows expression of anti-apoptotic proteins from Western blot analysis (left) quantified relative to Actin (right).

FIGS. 10A-10D show that therapeutic treatment with Leg-NP-CDDO modulates infiltration of immune cells into primary tumors. Mice were treated as depicted in FIG. 8A. Data represent means±s.e.m.

FIG. 10A shows flow cytometry results for tumors from treated mice 46 days after tumor cell challenge; live primary tumor single cell suspensions were analyzed by flow cytometry to detect activated CD8⁺ T cells.

FIG. 10B shows flow cytometry results for tumors from treated mice 46 days after tumor cell challenge; live primary tumor single cell suspensions were analyzed by flow cytometry to detect macrophages (B)

FIG. 10C shows flow cytometry results for tumors from treated mice 46 days after tumor cell challenge; live primary tumor single cell suspensions were analyzed by flow cytometry to detect dendritic cells.

FIG. 10D shows M1 macrophages identified in frozen tumor sections by immunohistochemistry using antibodies against F4/80 (grey) and NOS2 (white). Cell nuclei were stained with DAPI (black). Scale bar=100 μm.

FIGS. 11A-11C shows that Leg-NP-CDDO and pNeuTm combination therapy enhances anti-tumor immune surveillance and prevents breast cancer recurrence.

FIG. 11A show a schematic of treatment schedule for tumor recurrence study. Mice were challenged orthotopically with MMTV-Neu primary tumor cells (Day 0, black dashed arrow), treated with Leg-NP-CDDO or control NPs (gray solid arrows), and vaccinated with pNeuTm or pVector (gray dashed arrows). Primary tumors were surgically removed after reaching a size of ~500 mm³ (black solid arrow). Four weeks later, mice were re-challenged in the contralateral mammary fat pad with MMTV-Neu primary tumor cells (Day 53, black dashed arrow). Tumor dimensions were measured and used to calculate tumor size (n=5 mice/group). Data represent means±s.e.m.

FIG. 11B shows data from mice that were sacrificed when secondary tumors reached a volume of 500 mm³. Tumor free mice were sacrificed 128 days after initial tumor cell challenge. Splenocytes from pNeuTm vaccinated mice treated with either PBS, Leg-NP or Leg-NP-CDDO were cultured with irradiated MMTV-Neu primary tumor cells and analyzed by flow cytometry. Data represent means±s.e.m. *p<0.05.

FIG. 11C shows data for splenocytes from Leg-NP-CDDO/pNeuTM treated mice cultured with irradiated HEVc or MMTV-Neu primary tumor cells and analyzed by flow cytometry. HER-2 protein expression was confirmed by Western blotting. Data represent mean±s.e.m. ***p<0.0005.

DETAILED DESCRIPTION OF PREFERRED EMBODIMENTS

A novel NP targeting strategy is described herein, which utilizes a targeting moiety that binds to legumain, an asparaginyl endopeptidase. An aqueous tumor-targeting liposome nanoparticle composition comprises an aqueous dispersion of liposome nanoparticles. The nanoparticles preferably encapsulate an anti-cancer chemotherapeutic agent, which can be added to a pre-formed liposome composition or can be incorporated in the liposomes during the formation of the liposomes. The liposome nanoparticles comprise a legumain-targeting lipid admixed with one or more other micelle or vesicle-forming lipid materials in the form of a nanoparticulate liposome dispersion, preferably incorporating a polyethylene glycol-conjugated lipid. A preferred liposome nanoparticle composition comprises (a) a legumain-targeting lipid component, (b) a zwitterionic lipid component; (c) an amino-substituted lipid component; (d) a neutral lipid component; and (e) a polyethylene glycol-conjugated lipid component, e.g., a PEG-liposome composition. The legumain-targeting lipid component comprises a hydrophobic lipid portion covalently attached to a legumain-binding moiety.

Figure 4A:
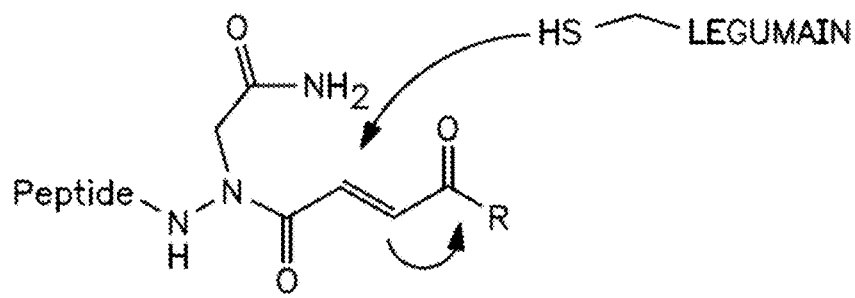
FIG. 4a schematically illustrates Michael addition of a legumain cysteine residue with an aza-Asn Michael acceptor.
Figure 4B:
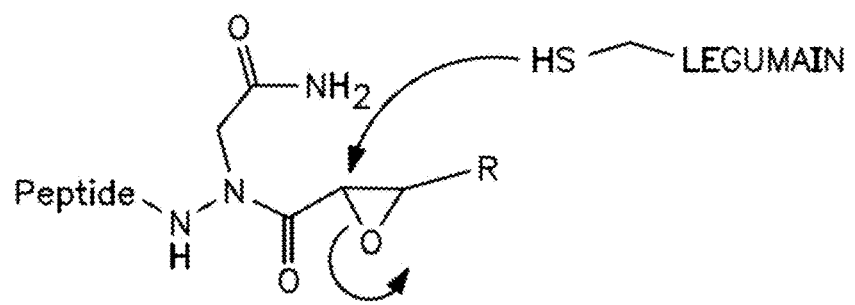
FIG. 4b shows the reaction of a legumain Cys residue with an aza-Asn-epoxide.
Figure 4C:
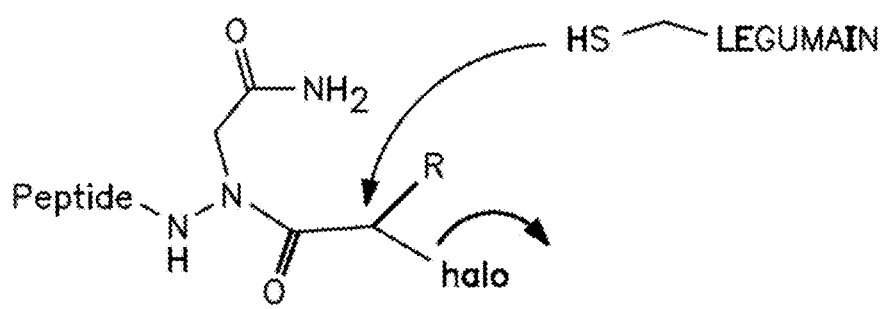
FIG. 4c shows the reaction of a legumain Cys residue with a aza-Asn-halomethylketone.
Figure 5A:
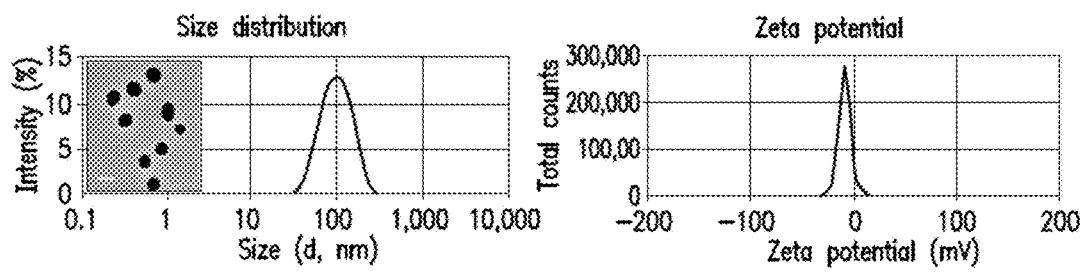
FIG. 5A shows physicochemical characterization of RR-11a-coupled NPs loaded with CDDO-Im analyzed by dynamic light scattering and TEM (inset) to determine particle size distribution (diameter, nm) and zeta potential (mV). Scale bar=100 nm.
Figure 5B:
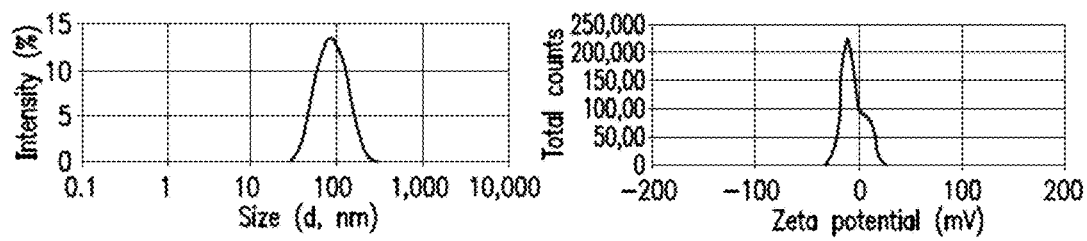
FIG. 5B shows physicochemical characterization of RR-11a-coupled NPs without CDDO-Im analyzed by dynamic light scattering and TEM (inset) to determine particle size distribution (diameter, nm) and zeta potential (mV). Scale bar=100 nm
Figure 5C:
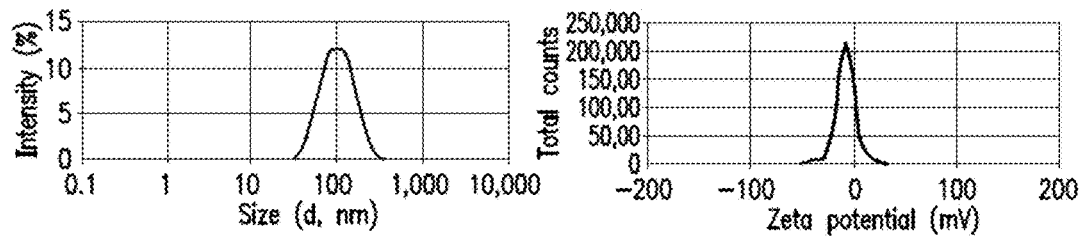
FIG. 5C shows physicochemical characterization of non-targeted NPs loaded with CDDO-Im analyzed by dynamic light scattering and TEM (inset) to determine particle size distribution (diameter, nm) and zeta potential (mV). Scale bar=100 nm.
Figure 5D:
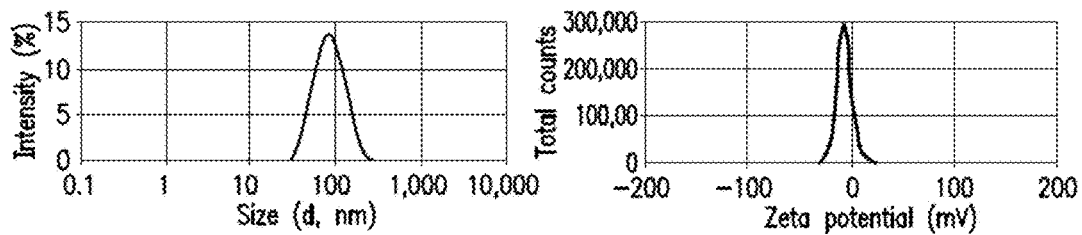
FIG. 5D shows physicochemical characterization of non-targeted NPs without CDDO-Im analyzed by dynamic light scattering and TEM (inset) to determine particle size distribution (diameter, nm) and zeta potential (mV). Scale bar=100 nm.

The legumain-binding moiety can be any material that selectively forms a stable complex or covalent bond with legumain, e.g., irreversible inhibitors of legumain, which typically comprise a peptide scaffold with affinity for legumain such as Ala-Ala-Asn (or Ala-Ala-X, where X is a modified Asn such as an aza-Asn residue) attached to a reactive functional group, e.g., aza-Asn-halomethylketones (see FIG. 4c), aza-Asn epoxides (see FIG. 4b), and aza-Asn Michael acceptors (see FIG. 4a) comprising an α,β-unsaturated carbonyl moiety as a Michael acceptor. Such aza-Asn moieties react with a cysteine residue at the legumain active site to form a covalent sulfide bond between the inhibitor and legumain, e.g., as shown in FIG. 4a-4c.

A preferred targeting moiety is represented by Formula (I):

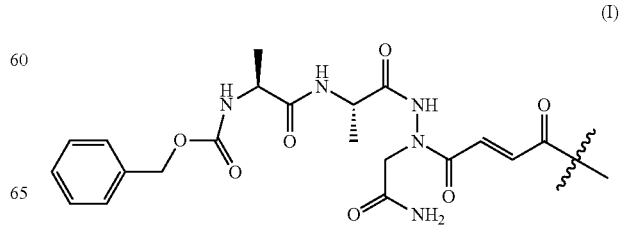

(I)

which is a synthetic aza-peptide Michael acceptor comprising two alanine residues attached to a modified aza-Asn moiety that includes an electron deficient double bond that acts as a Michael acceptor for a cysteine residue at the legumain active site. Formula (I) represents the core reactive portion of an aza-Asn Michael acceptor sometimes referred to as RR-11a. An N-hydroxysuccinimidoyl ester of RR-11a ("RR-11a-NHS") has the following structure:

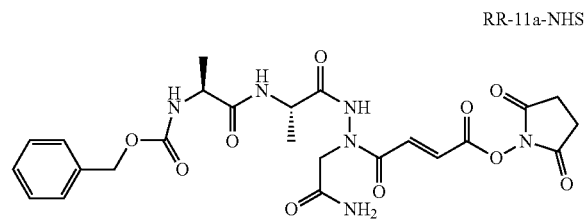 [SMILES: C[C@H](NC(=O)OCc1ccccc1)C(=O)N[C@@H](C)C(=O)NN(CC(N)=O)C(=O)/C=C/C(=O)ON1C(=O)CCC1=O]

RR-11a-NHS in which the carboxy terminal end of the RR-11a core is modified as a succinimidyloxy ester. The succinimidyloxy group of RR-11a-NHS is displaced by a phospholipid to form the legumain-targeting lipid component of the liposome nanoparticles described herein. For convenience, the structure of Formula (I) will be referred to herein as RR-11a in reference to legumain-targeting lipid materials.

A preferred legumain-targeting lipid comprises a compound of Formula (II):

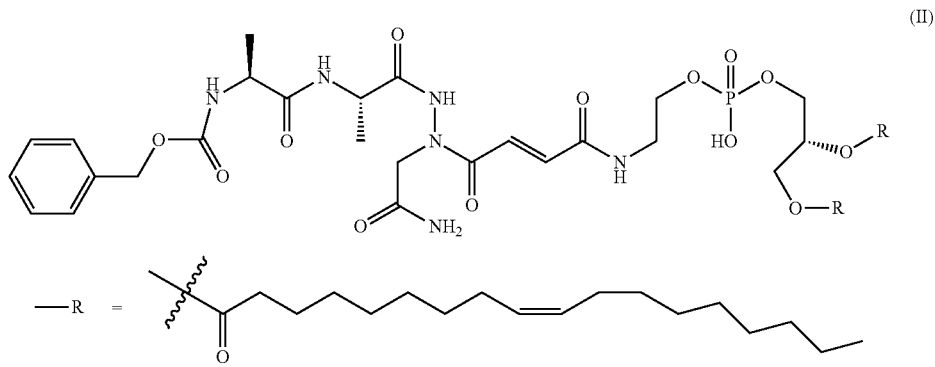

(II)

Cell-surface expression of legumain is driven by hypoxic stress, a hallmark of solid tumors, and polyethylene glycol (PEG)-coated liposomes, coupled to a legumain-targeting moiety such as RR-11a, show high ligand-receptor affinity, uptake and superior tumor penetration. An anti-cancer chemotherapeutic agent, such as doxorubicin, delivered by an RR-11a-conjugated PEG-liposome composition resulted in dramatically enhanced tumor selectivity, reduced drug sensitivity, and eliminated systemic drug toxicity.

Figure 1A:
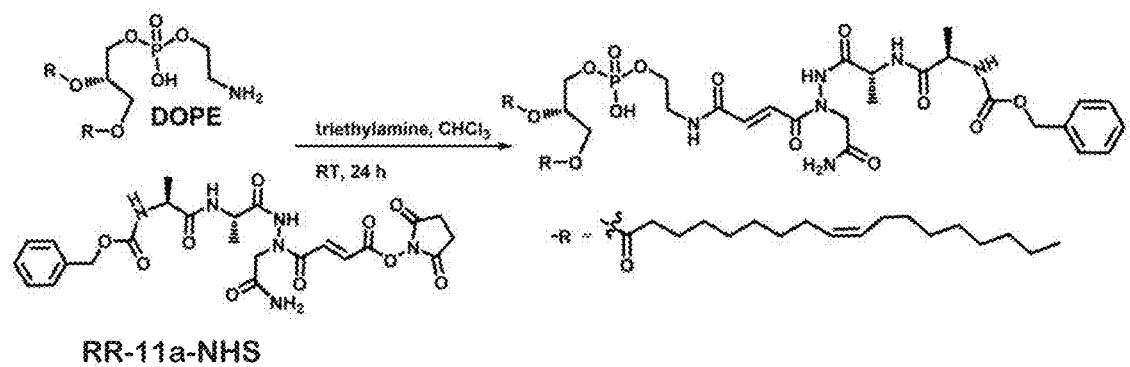
FIGS. 1a-1e illustrate the preparation and characterization of legumain-targeted nanoparticles (NPs).

The nanoparticle (NP) carrier portion of the targeted liposome compositions preferably comprises a membrane lipid such as a vesicle or other membranous structure, e.g., a liposome or a micelle capable of encapsulating an anti-cancer chemotherapeutic agent such as doxorubicin. Preferred NPs comprise a material having a hydrophobic lipid portion and a hydrophilic portion arranged such that liposomes or micelles will form when the material is dispersed in an aqueous system. FIG. 1a illustrates one preferred membrane lipid material (1,2-dioleoyl-sn-glycero-3-phosphoethanolamine, DOPE). The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of a phosphate, a phosphonate, a carboxylate, a sulfate, a sulfonate, a sulfhydryl, an amino, a nitro, a hydroxyl, or other like groups, which are well known in the art. Hydrophobicity can be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s).

Preferred micelle or vesicle-forming lipid materials suitable for attachment to the legumain-targeting agent are phosphoglycerides and sphingolipids. Representative examples of phosphoglycerides include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Compounds that lack phosphorous-containing groups, such as the sphingolipid and glycosphingolipid families, are also within the group designated as lipid. Additionally, the amphipathic lipids described above may be mixed with other lipids including triglycerides and sterols.

Other non-limiting examples of micelle or vesicle-forming lipid materials and other legumain-targeting lipid components are described in Example 7, below.

The legumain inhibitor/tumor-targeting agent can be attached to micelle or vesicle-forming lipid materials in the liposome nanoparticles at any suitable position, for example, at the termini of a linear chain or at any intermediate position thereof, as long as the attachment does not interfere with binding of the tumor-targeting agent to tumor expressed legumain. The tumor-targeting agent can also include, or be provided with, an optional divalent bridging group to facilitate attachment to the nanoparticles, if desired.

The compositions described herein can beneficially encapsulate any anti-cancer chemotherapeutic agent (e.g., an anti-tumor agent) for targeted delivery to legumain-expressing tumors. Such chemotherapeutic agents are described, for example, in Imai and Takaoka, Nat. Rev. Cancer 6, 714-726 (2006), which is incorporated herein by reference in its entirety. Non-limiting examples of such chemotherapeutic agents include: alkylating agents (e.g., cisplatin; carboplatin;

oxaliplatin; mechlorethamine; cyclophosphamide; chlorambucil; ifosfamide); purine and pyrimidine analogs and derivatives (e.g., 5-fluorouricil; floxuridine; cytosine arabinoside; mercaptopurine; thioguanine; azathioprine; fludarabine; pentostatin; cladribine); topoisomerase inhibitors (e.g., etoposide; etoposide phosphate; teniposide; amsacrine); taxanes (e.g., paclitaxel); antifolates (e.g., methotrexate; trimethoprim, pyrimethamine; pemetrexed); angiogenesis inhibitors (e.g., vitaxin; anecorvate, angiostatin; endostatin; squalamine; antiangiogenic tryptophanyl-t-RNA sythetase fragments, such as T2-TrpRS); anti-tumor monoclonal antibodies (e.g., bevacizumab; tivozanib; vandetanib; vatalanib; alemtuzumab; cetuximab; gemtuzumab; ibritumomab; pantitumumab; rituximab; tositumomab; trastuzumab); and other anti-neoplastic or chemotherapeutic agents, such as cytotoxic antibiotics (e.g., actinomycin; bleomycin; plicamycin; mitomycin); anthracycline antibiotics (e.g., doxorubicin; epirubicin; daunorubicin; valrubicin; idarubicin); triterpenoid Stat3 inhibitors (e.g., ursolic acid; a 2-cyano-3, 12-dioxooleana-1,9-dien-28-oic ester; a 2-cyano-3,12-dioxooleana-1,9-dien-28-oic amide such as 1-[2-cyano-3-,12-dioxooleana-1,9(11)-dien-28-oyl]imidazole (also known as CDDO-Im)); and the like, as well as physiologically acceptable salts and prodrugs thereof.

In some preferred embodiments, the chemotherapeutic agent is and anti-tumor agent that is an agonist or antagonist of a receptor or a receptor ligand involved in tumor growth.

The dosage regimens for the targeted-liposome/chemotherapeutic agent complexes or compositions containing the same, are based on several factors such as the age, weight, sex, and type of medical condition of the patient, the severity of the condition, the route of administration, and the binding activity of the particular targeting molecule employed. The dosage regimen may vary depending upon the aforementioned factors. Dosage levels on the order of about 0.01 milligram to about 1000 milligrams per kilogram of body weight are useful in treating the aforementioned medical conditions. Preferred dosage levels are in the range of about 0.01 milligram to about 100 milligrams per kilogram of body weight.

For administration by injection, a targeted-liposome/chemotherapeutic agent complex or composition containing the same is formulated with a pharmaceutically acceptable carrier such as water, saline, or an aqueous dextrose solution. For injection, a typical daily dose is about 0.01 milligram to about 100 milligrams per kilogram of body weight, injected daily as a single dose or as multiple doses depending upon the aforementioned factors.

The following non-limiting examples further illustrate certain aspects of the present invention.

EXAMPLE 1

Formulation and Characterization of Legumain-targeted nanoparticles

Nanoparticle Compositions. Synthesis of RR-11a has been described in the literature. See e.g., Ekici, O. D., et al. Aza-peptide Michael acceptors: a new class of inhibitors specific for caspases and other clan CD cysteine proteases. *J Med Chem* 47, 1889-1892 (2004) or Ovat, A., et al. Aza-peptidyl Michael acceptor and epoxide inhibitors, which are potent and selective inhibitors of *Schistosoma mansoni* and *Ixodes ricinus* legumains (asparaginyl endopeptidases). *J Med Chem* 52, 7192-7210 (2009). All phospholipids (Avanti Polar Lipids) were dissolved in chloroform. To achieve targeting, the carboxylic acid end of the aza-peptide was modified by activating this group with the 1-(3-dimethylaminopropyl)-3-ethylcarbodimide hydrochloride (EDC), followed by reaction with N-hydroxysuccinamide to produce the NETS-ester of RR-11a ("RR-11a-NHS"). RR-11a-conjugated NPs were generated by first, reaction of RR-11a-NHS with 1,2-dioleoyl-sn-glycero-3-phosphoethanolamine (DOPE) at approximately 1:1 molar ratio in the presence of triethylamine (TEA) for about 24 h at ambient room temperature (RT). Second, the resulting compound was combined with 1,2-di-(9Z-octadecenoyl)-sn-glycero-3-phosphocholine (DOPC), DOPE, cholesterol, and 1,2-dioleoyl-sn-glycero-3-phosphoethanolamine-N-[methoxy(polyethylene glycol)-2000](DOPE-PEG) at an approximate molar ratio of 1.1:6.7:6.7:2.2:1, as previously described for another liposome system. See: Hood, J. D., et al. Tumor regression by targeted gene delivery to the neovasculature. *Science* 296, 2404-2407 (2002). Size distribution was determined by dynamic light scattering on a ZETASIZER NANO® light scattering analyzer (Malvern).

Doxorubicin Loading into Nanoparticles. Doxorubicin was loaded into NPs as follows. Briefly, the lipid film was rehydrated in about 1 mL of sterile ammonium phosphate buffer (300 mM, pH 7.4) and agitated for a minimum of about 1 h followed by sonication to produce SUVs. The exterior ammonium phosphate buffer was exchanged with PBS (pH 7.4) by gel-filtration chromatography on NAP-10 columns (GE Healthcare). Doxorubicin in water was then added as a 10 mM solution and the mixture incubated overnight at RT. Finally, doxorubicin incorporated liposomes were purified by gel-filtration chromatography with NAP-10 columns using PBS (pH 7.4) buffer as an eluent. An RR-11a-conjugated liposome NP composition loaded with doxorubicin was designated as RDZ-218.

Figure 1B:
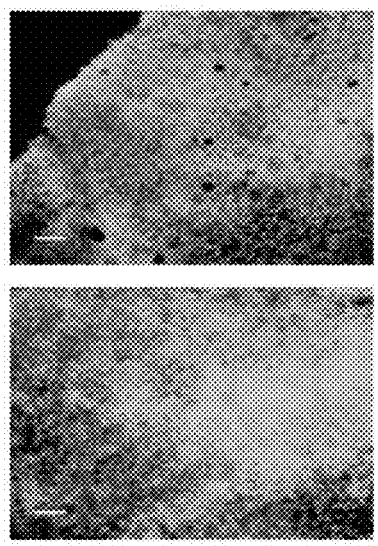
Figure 1C:
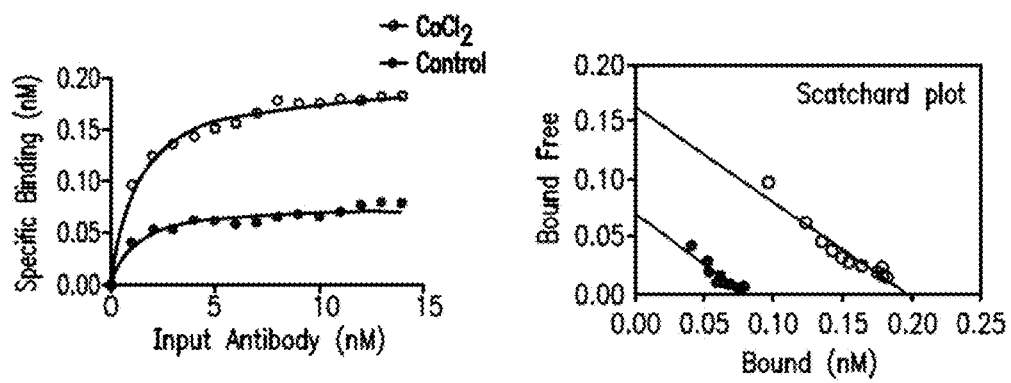
Figure 1D:
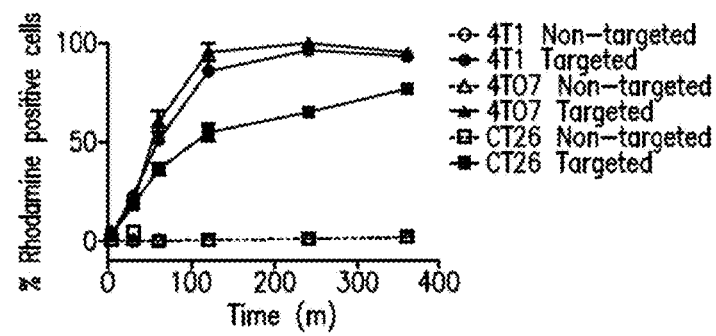
Figure 1E:
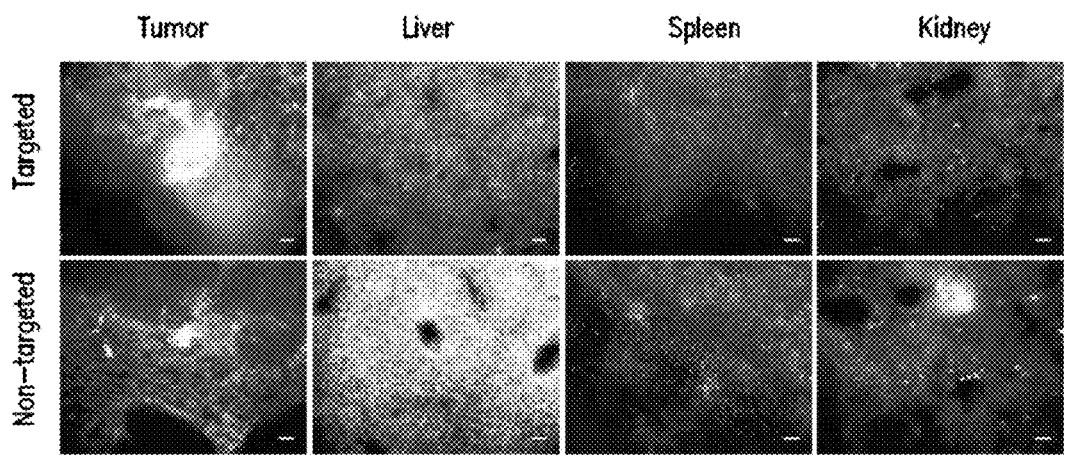

Conjugation of RR-11a to DOPE was achieved by first modifying the carboxylic acid end of the aza-peptide by activating this group with 1-(3-dimethylaminopropyl)-3-ethylcarbodimide hydrochloride (EDC), followed by reaction with N-hydroxysuccinamide to produce the NHS ester and coupling to the amino group of DOPE in chloroform, using triethylamine as a catalyst; see FIG. 1a. Tumor hypoxia was detected by staining with Glut-1 antibody and visualized using a fluorescein-conjugated secondary antibody. Cell nuclei were visualized by DAPI staining. Scale bars, 100 μm; see FIG. 1b. The affinity of anti-mouse legumain mAb for cell membrane-expressed legumain was determined by Scatchard analysis; see FIG. 1c. The mean Kd for control and $CoCl_2$ treated cells were calculated to be about 1.107±0.232 nM and about 1.208±0.107 nM, respectively. The number of binding sites for control and $CoCl_2$ treated cells were calculated to be about 46,760 and about 117,800 sites/cell, respectively. NPs were formulated in the presence of DOPE-rhodamine B lipid, which has red fluorescence. Murine 4T1 and 4TO7 breast and CT26 colon carcinoma cells were cultured for about 24 h with about 100 μM $CoCl_2$, after which RR-11a⁻ (Non-targeted) or RR-11a⁺ (Targeted) NPs were added to the cells; see FIG. 1d. After the times indicated, NPs were removed and the cells imaged immediately using fluorescence microscopy and the percentage of rhodamine B-positive cells quantified; n=3 wells per group. Data represent means±s.e.m. Female BALB/c mice with established orthotopic 4T1 breast tumors were injected once with Non-targeted or Targeted NPs. Mice were sacrificed about 24 h later and organs analyzed immediately by fluorescence microscopy to visualize distribution of NPs as indicated by rhodamine B fluorescence; n=2 mice per group; scale bars, 100 μm; see FIG. 1e.

EXAMPLE 2

Legumain-targeting enhances uptake of PEG-liposome-encapsulated doxorubicin and improves NP-mediated drug delivery to primary breast tumors Animals and cell lines. Female BALB/c mice were purchased from The Scripps Research Institute Rodent Breeding Facility. All animal experiments were performed according to the NIH Guide for the Care and Use of Laboratory animals and approved by The Scripps Research Institute Animal Care Committee. 4T1 and 4TO7 murine breast carcinoma cell lines were provided by Suzanne Ostrand-Rosenberg (University of Maryland, College Park, Md., USA). CT26 murine colon carcinoma cells were purchased from ATCC.

Binding study and Scatchard analysis. Anti-mouse legumain antibody (about 40 μg) (R&D Systems) was incubated for about 30 minutes (m) on ice with about 0.5 mCi of $^{125}$I (Amersham) in polystyrene tubes coated with about 100 μg of IODO-GEN® reagent (Pierce Chemical Co.). Non-incorporated $^{125}$I was removed by gel filtration on PD-10 columns (GE Healthcare). 4T1 cells ($5\times10^5$) were cultured with or without 100 μM $CoCl_2$ for about 24 hours (h), followed by incubation with about 14 nM serially diluted $^{125}$I-labeled antibody for about 2 h at about 4 μC. Cells were washed three times with PBS containing 1% bovine serum albumin (BSA), and the amount of bound radiolabel determined in a scintillation counter. The corresponding counts per minute (CPM) were used for Scatchard plot analysis with PRISM® software (GraphPad) and used to calculate the number of legumain binding sites.

In vitro nanoparticle uptake. Tumor cells were seeded at about $0.3\times10^6$ cells/well in a 6-well plate. About 24 h prior to addition of NPs, cells were treated with 100 μM cobalt chloride to stimulate hypoxia. RR-11a-conjugated or RR-11a-free NPs, either empty or loaded with 0.2 nM doxorubicin (Sigma), were added to the cells and incubated for about 15 and 30 m or about 1, 2, 3, 4 and 6 h, after which these cells were washed with PBS and fixed with 10% zinc formalin (Fisher Scientific) and immediately analyzed by fluorescence microscopy to visualize doxorubicin uptake. For analysis by flow cytometry, cells were trypsinized after removal of NPs, resuspended in FACS buffer, and immediately analyzed for mean fluorescence intensity.

Biodistribution assay. Mice bearing 4TO7 orthotopic tumors of approximately 500 $mm^3$ in size were injected i.v. with a single dose of RR-11a-conjugated NPs (RR-11a+) or RR-11a-free NPs (RR-11a$^-$) labeled with rhodamine B. Alternatively mice were injected three times at about 48 h intervals with either RDZ-218, NP-Dox, Free Dox, or PBS. About 24 h after the final treatment, animals were sacrificed and spleen, kidney, lungs, liver, heart and tumor were collected, frozen in OCT compound (Tissue-Tek) and immediately sectioned and imaged by fluorescence microscopy.

Statistical analysis. The statistical significance of differential findings between experimental groups and controls was determined by 2-tailed Student's t test using PRISM® software (GraphPad). Findings were regarded as significant if P<0.05.

Figure 2A:
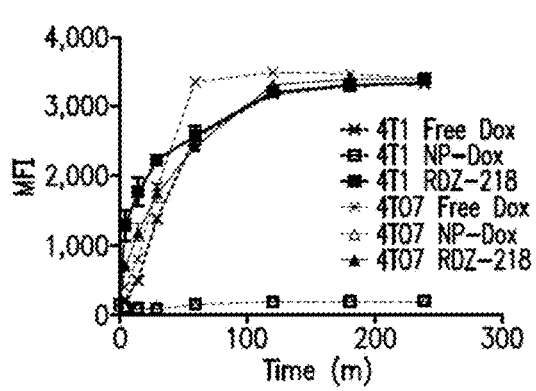
FIGS. 2a-2d demonstrate that legumain-targeting enhances uptake of PEG-liposome-encapsulated doxorubicin and improves NP-mediated drug delivery to primary breast tumors.
Figure 2B:
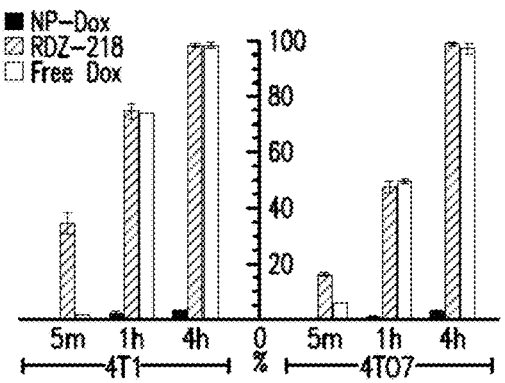

Doxorubicin was loaded into RR-11a$^+$ NPs using a phosphate gradient to generate RDZ-218. Doxorubicin was also loaded into RR-11a$^-$ NPs (NP-Dox) as a control. As illustrated in FIG. 2a, 4T1 and 4TO7 cells were cultured with $CoCl_2$ for about 24 h and then incubated with RDZ-218, NP-Dox or Free Dox for the indicated times, followed by flow cytometry analysis to determine mean fluorescence intensity (MFI) of doxorubicin; n=3 wells per group for each time point. Data represent means±s.e.m. The percentage of the drug uptake concentration was determined by comparing the MFI of RDZ-218, NP-Dox, and Free Dox-treated cells with that of serially diluted doxorubicin; see FIG. 2b. The relative percentage of dead 4T1 and 4TO7 cells approximately 24 h following treatment with either RDZ-218, NP-Dox, Free Dox, free RR-11a, or empty RR-11a$^+$ NPs (NP-RR-11a) was determined by analyzing the forward and side scatter plot of flow cytometry; see FIG. 2c. Data is shown relative to untreated cells (Control); n=3 wells per group. Data represent means±s.e.m. *p<0.05, **p<0.005. 4TO7 cells were injected into the inguinal mammary fat pad of female BALB/c mice. Tumors were allowed to establish for about 5 d, to a size of approximately 500 $mm^3$, after which mice were given two i.v. injections with RDZ-218, NP-Dox or Free Dox. Mice were sacrificed about 24 h after the last injection and tissues were isolated and immediately analyzed by fluorescence microscopy to detect distribution of doxorubicin; see FIG. 2d. Tissue sections were also stained with DAPI to visualize cell nuclei; n=2 mice per group; scale bars, 100 μm.

EXAMPLE 3

Therapeutic Treatment of Mice with RDZ-218 Results in Complete Suppression of Primary Breast Tumor Growth without Toxicity The thoracic mammary fat pads of female BALB/c mice were injected with about $1\times10^5$ 4TO7 cells. About 7 days after tumor cell challenge, mice were given 5 i.v. injections, at 3 d intervals, with either RDZ-218, NP-Dox, Free Dox (all at about 1 mg/kg Dox) or saline. Tumor dimensions were measured with microcalipers on each day of treatment and used to calculate tumor size. Mice were sacrificed about 24 h after the final treatment. Both the body and tumor weights were determined and tissues subject to histological analysis. TUNEL (Promega) staining was performed according to manufacturer's protocol.

Figure 3A:
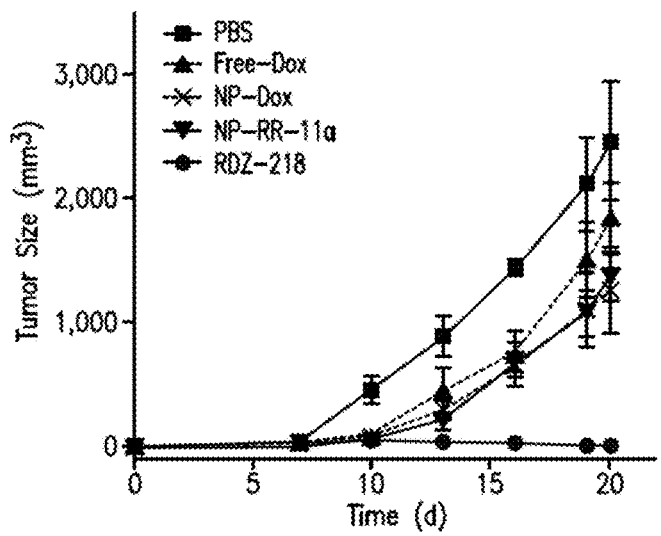
FIGS. 3a-3e demonstrate therapeutic treatment of 4TO7 tumor-bearing mice with RDZ-218 results in complete suppression of primary breast tumor growth without toxicity for mice treated with 5 i.v. injections of either RDZ-218, NP-Dox, free doxorubicin (Free Dox), empty RR-11a-conjugated NPs (NP-RR-11a), or phosphate-buffered saline (PBS) at 3-day intervals; data points represent treatment days; n=5 mice per group.
Figure 3B:
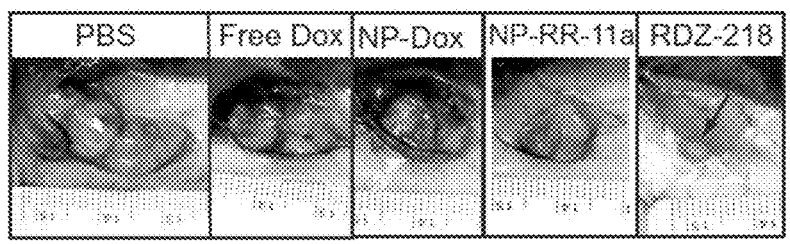
Figure 3C:
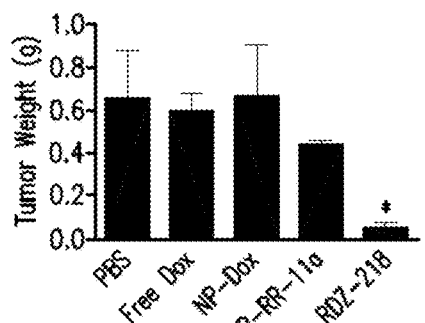
Figure 3D:
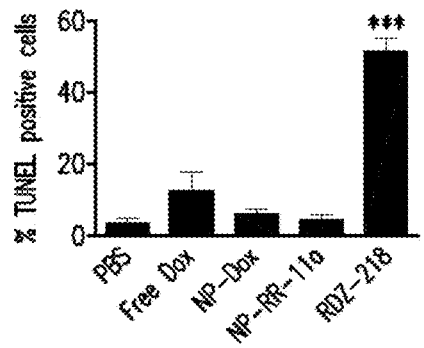

Female BALB/c mice were injected orthotopically with 4TO7 tumor cells and tumors allowed to establish for about 7 d prior to treatment. Mice were given 5 i.v. injections with either RDZ-218, NP-Dox, free doxorubicin (Free Dox), empty RR-11a$^+$ NPs (NP-RR-11a) or saline (PBS) at 3-day intervals. Data points represent treatment days; n=5 mice per group. On each day of treatment, tumor dimensions were measured with microcalipers and used to calculate tumor size; see FIG. 3a. Data represent means±s.e.m. Mice were sacrificed about one day after the 5th injection and images of primary tumors captured prior to dissection; see FIG. 3b. Images are representative from each group. The wet weight of primary tumors was also measured; see FIG. 3c. Data represent means±s.e.m; *p<0.05. Tumor sections were stained with TUNEL to visualize and quantify the percentage of apoptotic tumor cells; n=5 fields per section; see FIG. 3d. Data represent means±s.e.m; ***p<0.0005. The primary tumor weight was subtracted from the total body weight at time of sacrifice and compared to body weight prior to tumor cell challenge to determine change in body weight; see FIG.

3e. Data represent means±s.e.m. Control groups were compared to the RDZ-218 treated group, p=0.0029, *p<0.001.

EXAMPLE 4

Toxicity Evaluation

Female BALB/c mice bearing orthotopic 4TO7 tumors of approximately 500 mm$^3$ size were given 5 consecutive i.v. injections of free doxorubicin, NP-Dox, or RDZ-218 at approximately 24-hour intervals. The dose of doxorubicin for all groups was 5 mg/kg.

RDZ-218 shows no toxicity in vivo, in contrast to free and PEG-liposome-encapsulated doxorubicin of the prior art. Female BALB/c mice were injected orthotopically with 4TO7 breast tumor cells. Tumors were allowed to establish and reach a size of approximately 500 mm$^3$ prior to treatment. Mice were given 5 i.v. injections with either free doxorubicin (Free Dox), native (NP-dox) or RR-11a$^+$ PEG-liposome-encapsulated doxorubicin (RDZ-218). Doxorubicin was administered at about 5 mg/kg in 200 µl of PBS for all groups; n=5 mice per group. The results are shown in Table 1; fractions represent number of mice surviving, out of a total of 5, after each treatment.

TABLE 1

Toxicity Study of RDZ-218 in Treated Mice

| Treatment | 0 | 1 | 2 | 3 | 4 | 5 |
|---|---|---|---|---|---|---|
| Free Dox | 5/5 | 0/5 | — | — | — | — |
| NP-Dox | 5/5 | 5/5 | 3/5 | 1/5 | 1/5 | 1/5 |
| RDZ-218 | 5/5 | 5/5 | 5/5 | 5/5 | 5/5 | 5/5 |

Discussion

Ligand-targeting by conjugating PEG-liposome NPs to the small molecule inhibitor of legumain, RR-11a, from the class of aza-Asn Michael acceptor inhibitors is described herein; see FIG. 1a. RR-11a was designed with clan CD specific sequences and thus is highly specific for clan CD proteases, such as legumain, which it inhibits irreversibly at IC$_{50}$ values in the nanomolar range (IC$_{50}$=31-55 nM). Importantly, RR-11a does not interact with other related proteases, including caspases, clostripain or gingipain K, and is resistant to cleavage by proteases in vivo. The mechanism of legumain inhibition by RR-11a involves a nucleophilic attack by the catalytic cysteine residue on the Michael Acceptor double bond at C2, forming a covalent bond that irreversibly inhibits this asparaginyl endopeptidase; see FIG. 4a. In use the lipid nanoparticle compositions covalently bind RR-11a coupled NPs to legumain resulting in attachment of the entire liposomal composite to the receptor and subsequent irreversible internalization. This proposed mechanism is supported by NMR studies and is relevant since high binding affinity would improve NP targeting. Coupling of RR-11a to the 1,2-dioleoyl-sn-glycero-3-phosphoethanolamine (DOPE) component of NPs was achieved by reaction with triethylamine (TEA), see FIG. 1a. Analysis of RR-11a coupled PEG-liposome (RR-11a$^+$) or native PEG-liposome (RR-11a$^-$) NPs by dynamic light scattering revealed a uniform size distribution of approximately 150 and 110 nm, respectively (data not shown).

Legumain provides an excellent handle for tumor-targeting, since it is highly conserved between species, with about 83% homology between human and mouse legumain protein, and is over expressed in the majority of human solid tumors. Accordingly, Western blot analysis verified legumain protein expression in multiple murine carcinoma cell lines and a murine primary breast tumor, thus confirming previous reports. Although intracellular legumain is ubiquitously expressed, legumain expression on the cell surface occurs in response to microenvironment-induced cellular stress, such as serum starvation. Importantly, cell surface expression of legumain is enhanced by hypoxic stress, a hallmark of solid tumors, which is present in our orthotopic mouse model of breast cancer as determined by tumor expression of Glut-1, an established hypoxia-inducible protein; see FIG. 1b. Furthermore, in vitro immunohistochemical analyses of multiple murine carcinoma cell lines indicated that hypoxic stress induced cell surface expression of legumain (data not shown).

The efficiency of ligand-targeting depends, in part, on abundance of the target receptor, and is maximized by its over expression on target cells relative to normal cells. Thus, a restriction of ligand-targeting is the number of target cell surface receptors, which determines the number of molecules of targeting compound that can be specifically bound at the tumor site. Therefore, we quantified the number of legumain binding sites per tumor cell through binding studies and Scatchard plot analysis using $^{125}$I-labeled anti-legumain antibody. We calculated that under normal oxygen tension, the number of legumain binding sites were approximately 46,760 and under hypoxic conditions the number increased to about 117,800 sites/cell; see FIG. 1c. The fact that hypoxia induced about a 3-fold increase in number of tumor cell surface legumain binding sites is biologically relevant, since hypoxia is a hallmark of the solid tumor microenvironment, and thus frees the targeting system from dependence on any single genetic characteristic of the tumor. Therefore, targeting strategy described herein should not be limited by the genetic heterogeneity commonly observed in solid tumors.

To evaluate the extent to which RR-11a coupling enhances uptake of PEG-liposome NPs by tumor cells in vitro, murine breast (4T1 and 4TO7) and colon (CT26) carcinoma cells, subjected to hypoxic stress, were incubated at varying time points with RR-11a$^+$ or RR-11a$^-$ NPs labeled with the fluorescent dye rhodamine B. Analysis by fluorescence microscopy revealed markedly enhanced uptake of RR-11a$^+$ NPs, compared to RR-11a$^-$ NPs, in all three cell lines at all time points tested; see FIG. 1d. The efficacy of in vivo targeting was determined by i.v. injection of these same particles into female BALB/c mice bearing orthotopic 4T1 breast tumors of approximately 500 mm$^3$ size. Fluorescence microscopy of tumor and tissues from these animals revealed a marked increase of RR-11a$^+$ NPs homing to primary tumors and reduced non-specific accumulation in organs of the reticuloendothelial system (RES), including liver, spleen and kidney, when compared with RR-11a$^-$ NPs; see FIG. 1e. Unexpectedly, the marked decrease in accumulation of RR-11a$^+$ NPs observed in the liver is significant since this RES organ has been identified as a major sink for non-targeted PEG-liposome NPs, which may result in liver toxicity. Together, these surprising data indicate that coupling of RR-11a to PEG-liposome NPs enhances their uptake by tumor cells under hypoxic stress and effectively increases homing of NPs to primary tumors while reducing accumulation in RES organs.

An important factor for effective ligand-mediated NP drug delivery is not only their ability to carry an optimal payload to the desired target cell, but also to effectively release this payload following delivery. To critically evaluate these parameters, doxorubicin, a chemotherapeutic drug commonly used to treat breast cancer, was loaded into NPs via an ammonium phosphate gradient, as previously described. Murine breast tumor cells (4T1 and 4TO7) under hypoxic stress were then incubated with either free doxorubicin (Free Dox), or doxorubicin-loaded RR-11a$^-$ (NP-Dox) or RR-11a$^+$ (RDZ-218) NPs at various time points, and analyzed immediately by flow cytometry to quantify the mean fluorescence intensity (MFI) of doxorubicin internalized by the cells. RDZ-218 treated cells showed enhanced uptake of doxorubicin when compared with cells treated with NP-Dox; see FIG. 2a. Surprisingly, treatment with RDZ-218 not only resulted in more rapid drug uptake over time compared to NP-Dox, but also increased the degree of uptake by as much as about 16-fold, with the rate of RDZ-218 uptake similar to that of Free Dox; see FIG. 2a. By comparing the MFI generated from cells treated with serially diluted free doxorubicin to that of cells treated with NP encapsulated doxorubicin, we were surprised to observe that close to 100% of RDZ-218 NPs were taken up by the cells within about 4 hours of treatment; see FIG. 2b. Furthermore, the immediate and rapid uptake of RDZ-218, compared with Free Dox, was indicative of ligand-receptor-mediated internalization, and was superior when compared to non-targeted NP-Dox.

Figure 2C:
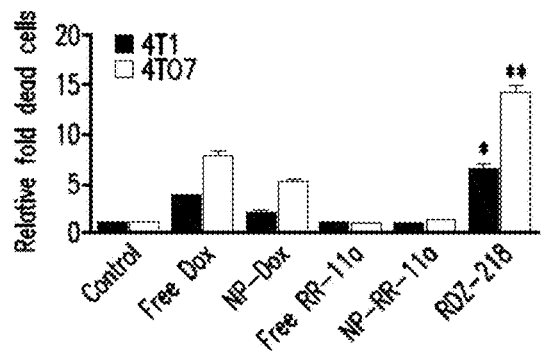
Figure 2D:
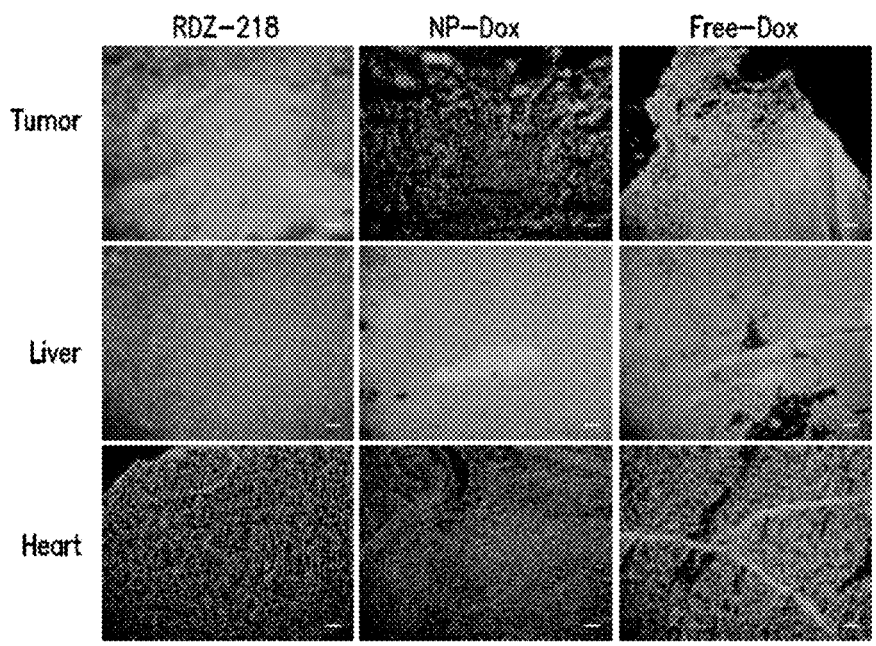

Next, doxorubicin bioactivity of RDZ-218 was determined in vitro with flow cytometry by comparing the percentages of dead tumor cells about 24 hours following treatment; see FIG. 2c. Cells treated with RDZ-218 showed a 3 to 15-fold increase in the percentage of dead cells compared to control or NP-Dox treated cells. Intriguingly, this cytotoxic effect of RDZ-218 was better than that of Free Dox. Importantly, no cytotoxic effect was observed in cells treated with free RR-11a or empty RR-11a$^+$ NPs, indicating that the enhanced cytotoxicity observed with RDZ-218 is due to increased NP-mediated doxorubicin uptake, and not to any effects of legumain inhibition by RR-11a on tumor cells. Collectively, these results demonstrate that RDZ-218 enhances delivery of a biologically effective drug payload to tumor cells in vitro.

The main therapeutic objective of ligand-targeted NP delivery is to minimize undesirable systemic drug toxicities arising from non-specific accumulation of NPs in RES organs, while still being able to deliver a biologically effective dose of drug to target cells. However, one concern with using NPs for drug delivery is that NPs are relatively larger than drug molecules and thus would be less likely to penetrate the vascular wall and gain access to tumor cells compared to small molecular mass drugs or antibodies. Therefore, to test the ability of RDZ-218 to effectively and specifically deliver a drug payload to the target tissue in a therapeutic setting, mice with established breast tumors, of approximately 500 mm$^3$ in size, were given two i.v. injections of either RDZ-218, NP-Dox, or Free Dox approximately 48-hour intervals. Microscopic analysis of tumors about 24 h after the last injection revealed intense and widely spread doxorubicin fluorescence in tumors from RDZ-218 treated animals; see FIG. 2d. In contrast, doxorubicin fluorescence was strikingly reduced or punctate in tumors from mice treated with either NP-Dox or Free Dox; see FIG. 2d. Surprisingly, only mice treated with RDZ-218 showed markedly reduced doxorubicin fluorescence in the liver and heart when compared with NP-Dox and Free Dox treated mice, respectively; see FIG. 2d. The reduction in doxorubicin accumulation in the heart is particularly important since cardiotoxicity is a dose-limiting factor for doxorubicin therapy. These results clearly indicate that RDZ-218 has tumor penetrating ability and that RR-11a$^+$ NPs can achieve specific delivery of a drug payload to solid tumors in vivo, while reducing non-specific accumulation of drug in peripheral organs such as liver and heart.

Figure 3E:
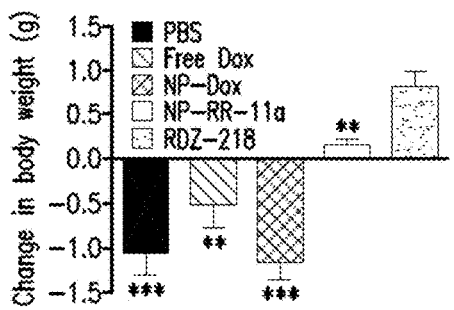

The therapeutic efficacy of the doxorubicin payload delivered by RR-11a$^+$ NPs to mice with established breast tumors was evaluated by giving them 5 i.v. injections of either RDZ-218, NP-Dox, empty RR-11a$^+$ NPs (NP-RR-11a), Free Dox, or saline at 3-day intervals. Determination of tumor size with microcalipers revealed that RDZ-218 treatment alone essentially eradicated tumor growth, whereas control groups only delayed tumor growth, compared to saline treated animals; see FIG. 3a. Three weeks after tumor cell challenge, gross examination of primary tumors from mice treated with RDZ-218 revealed only rudimentary tumor nodules while control mice had large tumor masses of approximately 500 mm$^3$ in size or greater; see FIG. 3b. Treatment with RDZ-218 resulted in an approximately 8 to 12-fold decrease in tumor weight when compared with controls; see FIG. 3c. Concordantly, TUNEL immunohistochemical analysis of tumor sections from RDZ-218 treated mice revealed between a 9 to 35-fold increase in percentage of apoptotic cells when compared to tumors from control animals; see FIG. 3d. Surprisingly, mice treated with RDZ-218 did not show any loss in body weight over the course of the study, which is indicative of reduced toxicity; see FIG. 3e.

To confirm this reduced toxicity of RDZ-218, a toxicity study was performed in tumor bearing mice by daily administration of a single dose of Free Dox, NP-Dox or RDZ-218, at about 5 mg/kg doxorubicin for all groups, over the course of about 5 days (Table 1). Only the RDZ-218 treated group had all animals surviving after the final treatment on day 5. In contrast, Free Dox administered at about 5 mg/kg was lethal, and all test animals in this group expired immediately following the first treatment. In comparison, the non-targeted NP-Dox treated group had only one animal surviving after the completion of all 5 treatments, with lethal toxicity observed after the 2nd and 3rd treatments in 4 of 5 animals. These surprising results confirm that RR-11a-mediated ligand-targeting of PEG-liposomes reduces non-specific accumulation of doxorubicin in non-target organs, thus eliminating lethal systemic toxicity.

EXAMPLE 5

Legumain-targeting NP encapsulated CDDO-Im

CDDO-Im was incorporated into the NPs by taking advantage of the physical characteristics of CDDO-Im, namely, its hydrophobicity and chemical similarity to cholesterol, to assure spontaneous incorporation of CDDO-Im into the lipid bilayer upon rehydration of the lipid film. Addition of a 0.6 molar ratio of CDDO-Im to DOPE:DOPC:cholesterol:DOPE-PEG:DOPE-RR-11a at molar ratios of 6.7:6.7:2.2:1:1.1, respectively, resulted in effective loading of CDDO-Im. Analysis by UV spectrometry of free CDDO-Im and encapsulated CDDO-Im, after release by NP disruption indicated a loaded concentration of about 45 micromol/L CDDO-Im, which is approximately 450-fold more concentrated than the dose of 100 nmol/L required for effective Stat3 inhibition. Analysis of NPs by dynamic light scattering and TEM showed an optimal average NP diameter of about 100 nm and a zeta potential close to 0 (See FIG. 5A-5D).

EXAMPLE 6

In Vivo Evaluation of Encapsulated CDDO-Im

Materials. Authenticated 4TO7/4T1 murine breast carcinoma cells were provided by Suzanne Ostrand-Rosenberg (University of Maryland, College Park, Md.) and maintained in RPMI-1640 medium (Gibco, Carlsbad, Calif., USA) supplemented with 10% FBS, 1% HEPES, 1% sodium bicarbonate and 1% sodium pyruvate. Cell lines are authenticated by in vivo growth/metastasis in Balb/c mice, by expressions of IL-6 and S100A8/A9, and resistance to 6-thioguanine. Cells were tested negative for *mycoplasma* using MycoALERT (2008, Lonza, Basel, Switzerland). MMTV-Neu primary tumor was provided by Michael Karin (University of California, San Diego, Calif., USA) and maintained by serial passage in syngeneic FVB/NJ mice. Briefly, MMTV-Neu primary tumors were minced and digested under sterile conditions with Type 3 Collagenase (Worthington, Lakewood, N.J., USA) in RPMI-1640 medium supplemented with 2.5% FBS and 10 mM Hepes. $1 \times 10^6$ cells were resuspended in PBS and injected into the mammary fat pad of syngeneic female FVB/NJ mice. This procedure was repeated once primary tumors reached a size of approximately 500 mm$^3$.

Western blot. Protein extracts were prepared as previously described. Western blots were probed with the following antibodies: rabbit anti-phospho-STAT-3 (Cell Signaling, Danvers, Mass., USA), goat-anti-β-actin, IL-6 and IL-10, rabbit-anti-phospho-STAT-1, STAT-3, IL-2, Bcl-x$_L$, Bcl-2 and TGF-β, rat-anti-IL-12b, GM-CSF and IFN-γ, and mouse-anti-IL-15 (all Santa Cruz Biotechnology, Santa Cruz, Calif., USA) and anti-ERBB2 (Abcam, Cambridge, Mass., USA). Protein band intensities were quantified using ImageJ software and normalized to β-actin.

In vivo tumor studies. 4TO7 ($5 \times 10^3$) cells or MMTV-Neu ($1 \times 10^4$) primary tumor cells were injected orthotopically into female BALB/c or FVB/NJ mice, respectively. NPs in 200 µl of PBS (about $1.36 \times 10^{13}$ particles) were administered i.v. and tumor dimensions measured using digital microcalipers. Tumor volume was calculated using the formula [(a$^2 \times$b)/2], where 'a' is the larger of two perpendicular diameters. For recurrence studies, primary tumors were surgically removed and mice re-challenged orthotopically in the contralateral mammary fat pad. Mice were vaccinated 3 times orally at 1 week intervals by gavage with attenuated *salmonella* typhimuirum ($1 \times 10^8$ CFU per mouse) transduced with either pNeuTm (provided by Wei-Zen Wei, Karmanos Cancer Center, Detroit, Mich., USA) or empty vector.

Flow cytometry. Splenocytes and tumor infiltrating lymphocytes were isolated and incubated ($1 \times 10^6$ cells per tube) with fluorescein-conjugated antibodies (0.25 µg antibody per $10^6$ cells in 100 µl volume) against mouse CD8, CD25, CD14, CD11c, CD11b, CD80, CD45, F4/80 (Biolegend, San Diego, Calif. USA) and/or Granzyme B (0.125 µg antibody per $10^6$ cells in 100 µl volume) (eBioscience, San Diego, Calif., USA). Data were collected on a digital LSR-II (Becton Dickinson, Franklin Lakes, N.J., USA) and analyzed with FlowJo software (Tree Star, Inc., Ashland, Oreg., USA).

Immunohistochemistry. Tumor sections fixed in acetone were stained with the following primary antibodies: rat anti-mouse F4/80 (1:50 dilution, AbD Serotec, Raleigh, N.C., USA) and rabbit anti-mouse Nos2 (1:50 dilution, Santa Cruz Biotechnology, Santa Cruz, Calif., USA), and detected with the following secondary antibodies: goat anti-rat IgG Alexa Fluor 568 or goat anti-rabbit IgG Alexa Fluor 488 (both at 1:200 dilution, Molecular Probes, Carlsbad, Calif., USA), respectively. For staining controls, tissue sections were incubated with secondary antibodies only. Cell nuclei were stained with DAPI-dilactate (Sigma, St. Louis, Mo., USA).

Figure 6A:
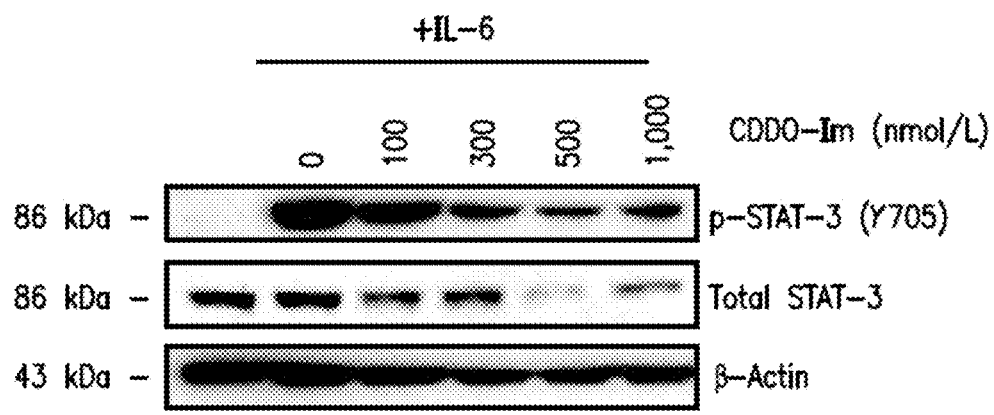
FIGS. 6A-6C show that encapsulated CDDO-Im inhibits STAT-3 phosphorylation in murine breast cancer cells and primary tumors by Western Blot analysis.
Figure 6B:
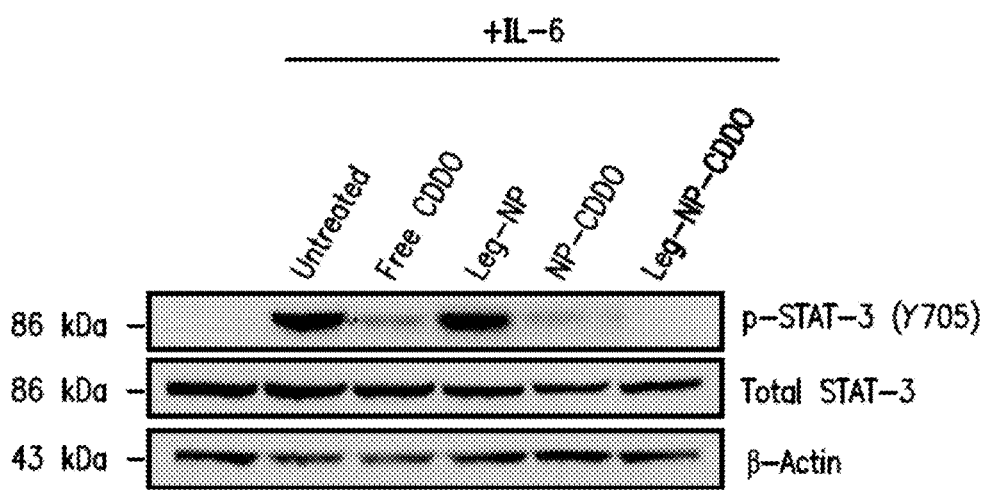

CDDO-Im inhibits STAT-3 activation in murine breast cancer cells. The ability of CDDO-Im to inhibit IL-6-induced STAT-3 activation in murine breast cancer cells was evaluated by incubating 4T1 tumor cells with IL-6 and increasing concentrations of free CDDO-Im. Western blot analysis revealed that CDDO-Im blocked STAT-3 phosphorylation and suppressed expression of total STAT-3 protein at 100 nM-1 µM concentrations (FIG. 6A). The ability of encapsulated CDDO-Im to inhibit STAT-3 activation was confirmed by incubating IL-6 stimulated 4TO7 tumor cells with empty targeted NPs (Leg-NP), non-targeted (NP-CDDO) or targeted (Leg-NP-CDDO) NPs loaded with CDDO-Im, or free CDDO-Im. Western blot analysis showed that encapsulated CDDO-Im blocked STAT-3 phosphorylation as well as free CDDO-Im (FIG. 6B). Importantly, cells treated with Leg-NP did not show inhibition of STAT-3 phosphorylation, thus demonstrating that inhibition was due solely to CDDO-Im and not by any non-specific effect of NPs (FIG. 6B).

Figure 6C:
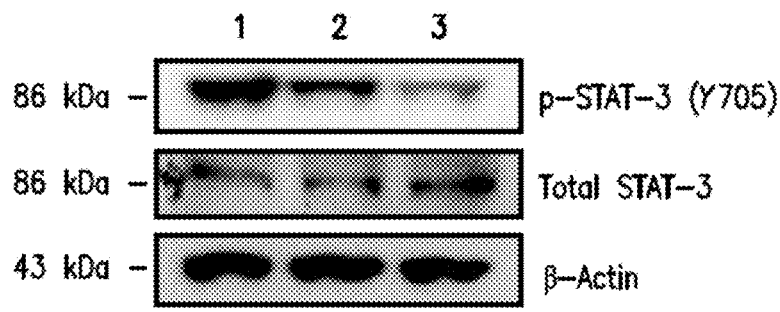

Finally, the ability of Leg-NPs to deliver a CDDO-Im payload to MMTV-Neu primary tumors in a therapeutic setting was tested. To this end, mice bearing orthotopic breast tumors were given 8 i.v. injections at 3 day intervals with either saline (PBS), Leg-NP or Leg-NP-CDDO. Western blot analysis of MMTV-Neu primary tumor protein extracts obtained one day after the last injection showed that Leg-NP-CDDO effectively inhibited STAT-3 phosphorylation in primary tumors (FIG. 6C). Collectively, these data demonstrate that CDDO-Im inhibits STAT-3 phosphorylation in murine breast cancer cells. Additionally, this work demonstrates successful encapsulation of CDDO-Im into liposomal NPs for targeted delivery to the TME and effective therapeutic inhibition of STAT-3 phosphorylation in vivo.

Figure 7A:
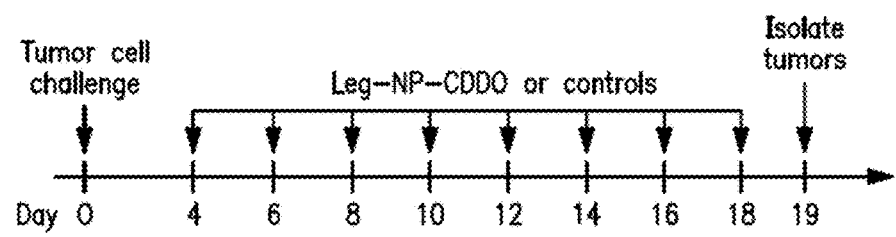
FIGS. 7A-7C show that therapeutic treatment with Leg-NP-CDDO inhibits growth of 4TO7 tumors.
Figure 7B:
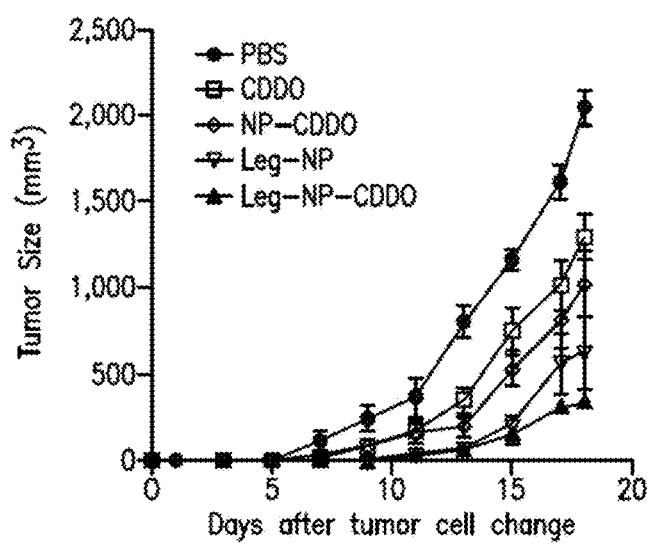
Figure 7C:
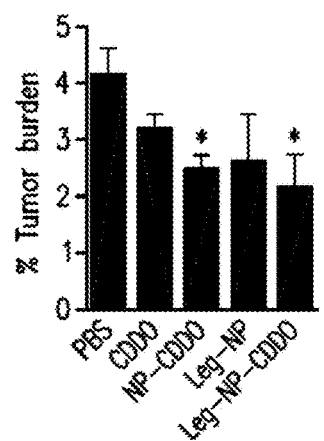

Leg-NP-CDDO suppresses growth of murine breast tumors. To evaluate the in vivo effects of Leg-NP-CDDO, BALB/c mice were orthotopically challenged with about $5 \times 10^3$ 4TO7 tumor cells and 4 days later, treated them with 8 i.v. injections of Leg-NP-CDDO or controls (FIG. 7A). Primary tumor growth was significantly suppressed by Leg-NP-CDDO when compared with controls (FIG. 7B). Importantly, treatment with free CDDO-Im or CDDO-Im encapsulated in non-targeted particles was markedly less effective at suppressing tumor growth when compared with Leg-NP-CDDO. Additionally mice treated with Leg-NP-CDDO showed a significant decrease in tumor burden compared with untreated controls (FIG. 7C).

Figure 8A:
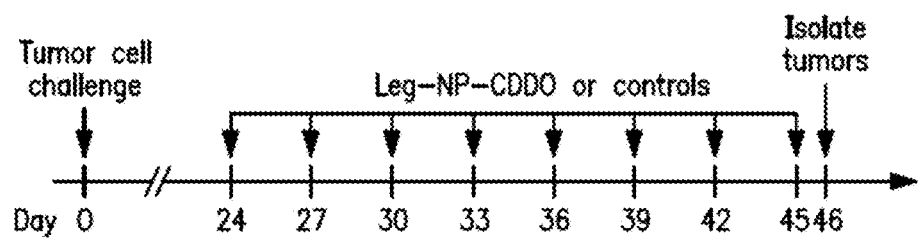
FIGS. 8A-8C show that therapeutic treatment of MMTV-Neu primary tumors with Leg-NP-CDDO delays tumor growth.
Figure 8B:
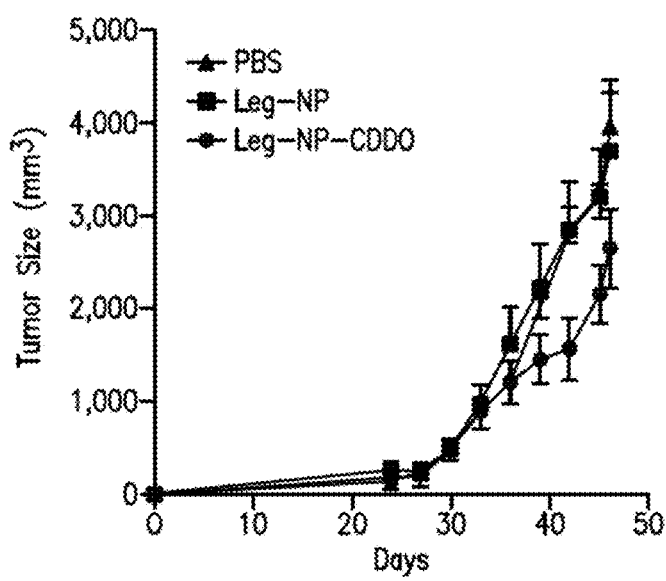
Figure 8C:
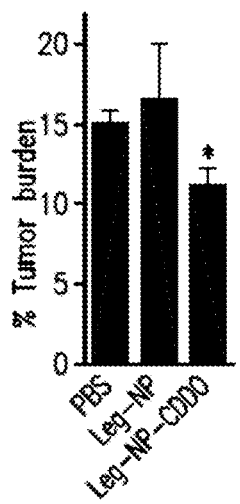

However, compared with primary tumor cells, established tumor cell lines, such as 4TO7, that have been in long term culture ex vivo may acquire genetic and phenotypic changes which may affect their therapeutic response. Therefore, to critically evaluate the efficacy of Leg-NP-CDDO, mice were treated with orthotopic tumors derived from MMTV-Neu primary cells with 8 i.v. injections of Leg-NP-CDDO, Leg-NP, or PBS (FIG. 8A). Calculation of tumor volumes revealed that mice treated with Leg-NP-CDDO showed only marginally reduced tumor size compared with controls (FIG. 8B), despite significantly reduced tumor burden (FIG. 8C). Therefore, Leg-NP-CDDO was markedly less effective at suppressing in vivo growth of primary tumor cells compared to tumors derived from 4TO7 cell lines.

Figure 9A:
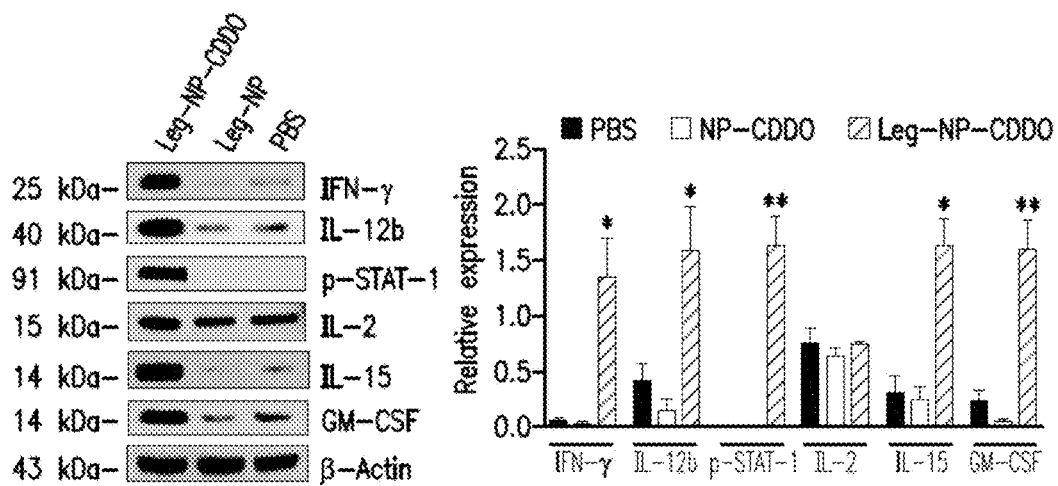
FIGS. 9A-9C show that Leg-NP-CDDO modulates tumor cytokine and growth factor expression profiles in vivo. Whole tissue extracts were prepared from MMTV-Neu primary tumors isolated from mice treated as described in FIG. 8A. Western blot analyses (left panels) were performed and quantified relative to Actin (right graphs) to determine protein expression of Th1 and Th2 associated growth factors and cytokines. Additionally, expression of anti-apoptotic proteins was also determined. Data represent means±s.e.m. from 3 independent experiments. *p<0.05 and **p<0.005.
Figure 9B:
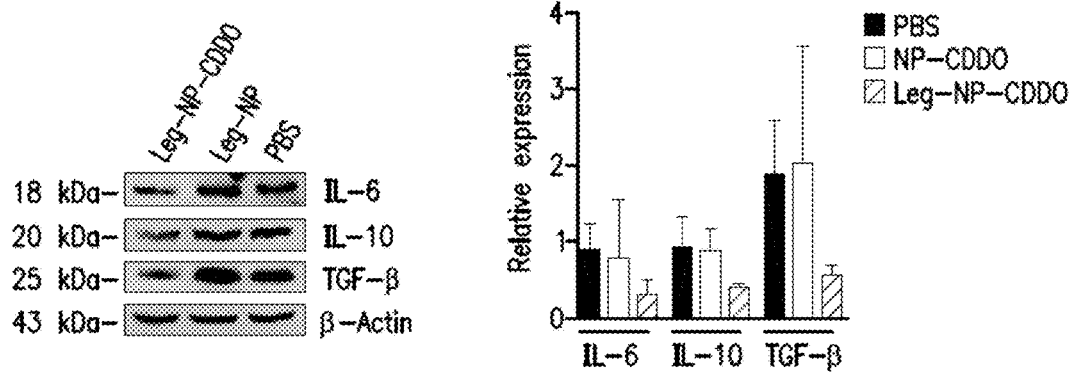
Figure 9C:
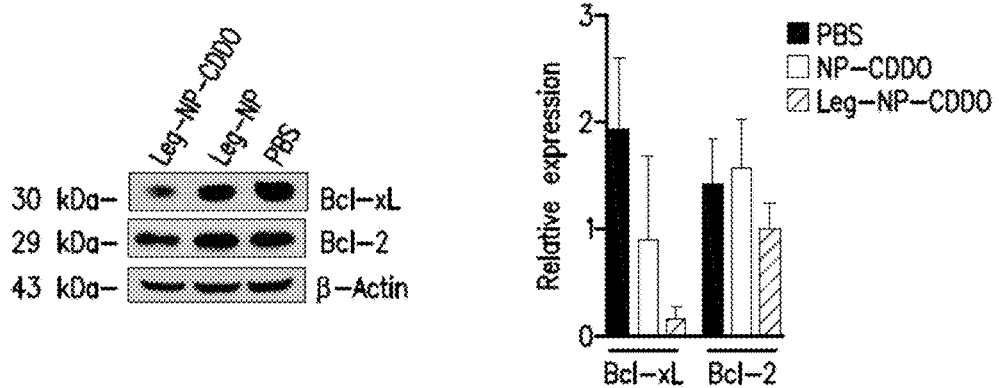

Leg-NP-CDDO modulates cytokine and growth factor expression in primary tumors. STAT-3 signaling mediates tumor-associated immune suppression in vivo by modulating cytokine and growth factor expression by tumor cells and other cells in the TME, including macrophages. Therefore, to evaluate the effects of Leg-NP-CDDO on expression levels of these factors, whole cell extracts were derived from primary tumors of mice treated with Leg-NP-CDDO, Leg-NP or PBS. Western blot analysis showed markedly upregulated protein expressions of pSTAT-1 (715-fold), IL-15 (37-fold), IL-12b (9-fold), IFN-γ □ (24-fold) and GM-CSF (6-fold) in mice treated with Leg-NP-CDDO as compared with controls (FIG. 9A). Conversely, protein expressions of IL-6, IL-10 and TGF-β showed a 2 to 5-fold decrease in primary tumors of Leg-NP-CDDO treated mice (FIG. 9B). Leg-NP-CDDO treatment also downregulated expressions of anti-apoptotic proteins Bcl-$X_L$ (8-fold) and Bcl-2 (1.4-fold) (FIG. 9C). Intriguingly, these results indicate a Th1 cytokine polarization of the TME as a result of Leg-NP-CDDO therapy.

Figure 10C:
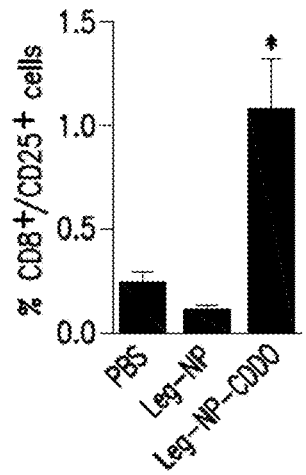
Figure 10C:
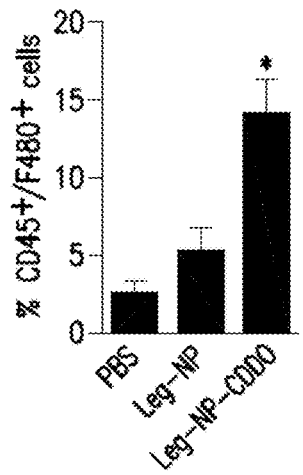
Figure 10C:
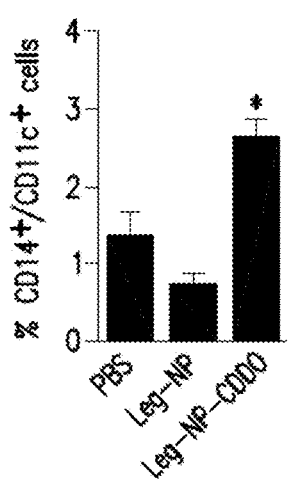
Figure 10C:
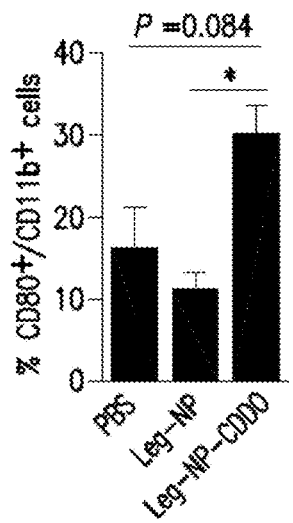

Increase in antigen presenting cells and $CD8^+$ T cells in primary tumors of Leg-NP-CDDO treated mice. Immune cells recruited by tumors secrete different cytokines and growth factors depending upon whether they receive Th1 or Th2 polarizing signals from the TME. Therefore, the Th1 shift that was observed in cytokine expression suggested that changes in the immune cell milieu in tumors might also be evident. To evaluate this hypothesis, live single cell suspensions of primary tumors were derived from mice treated with either Leg-NP-CDDO, Leg-NP or PBS and analyzed by flow cytometry to detect activated $CD8^+$ T cells, DCs and macrophages (FIG. 10 A-C). Mice treated with NP-Leg-CDDO showed a 4.6-fold increase in $CD8^+/CD25^+$ T cells compared with PBS controls (FIG. 10A). Additionally, mice treated with Leg-NP-CDDO revealed a 5.6 and 2-fold increase in macrophages ($CD45^+/F4/80^+$) (FIG. 10B) and DCs ($CD14^+/CD11c^+$ and $CD80^+/CD11b^+$) (FIG. 10C), respectively.

Figure 10D:
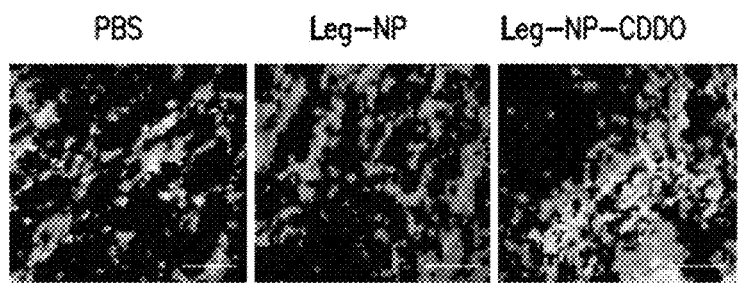

Macrophages have very different effects on immune function and tumor growth depending on their mode of activation and polarization. 'Classically activated' M1 macrophages typically show high expression of NOS2 in association with anti-tumor immune responses. In contrast, 'alternatively activated' M2 macrophages do not express NOS2 and are typically associated with immune suppression and pro-tumor responses. Therefore, an investigation was made as to whether macrophages in primary tumors of Leg-NP-CDDO treated mice corresponded to either M1 or M2. To this end, immunohistochemistry and fluorescence microscopy analysis of tumors revealed a marked increase in $F4/80^+/Nos2^+$ positive cells in tumors derived from Leg-NP-CDDO treated mice (FIG. 10D), whereas control tumors showed robust $F4/80^+$ staining that was predominantly $NOS2^-$ (FIG. 10D). These findings suggest that M1 polarization of tumor infiltrating macrophages is a result of Leg-NP-CDDO treatment.

Combination therapy improves the anti-tumor effects of a Her-2 DNA vaccine.

The present findings suggest that treatment with Leg-NP-CDDO blocks TME-mediates immune suppression. Furthermore, based on cytokine expression profiles and immune effector cell infiltration, the immune TME appeared sufficiently primed for an anti-tumor response. FVB/NJ mice were challenged orthotopically with about $1 \times 10^4$ MMTV-Neu primary tumor cells and treated with a combination of Leg-NP-CDDO and a DNA vaccine against the extracellular domain of HER-2 (pNeuTM) (FIG. 11A). Alternatively, mice were also treated with empty targeted NPs (Leg-NP) or a control vaccine (pVector). Primary tumors were surgically removed after reaching a volume of 500 mm³, and after 4 weeks of recovery, mice were re-challenged with about $1 \times 10^4$ MMTV-Neu primary tumor cells in the contralateral fat pad for experimental recurrence. Tumor recurrence was significantly suppressed in mice treated with the Leg-NP-CDDO/pNeuTm combination therapy, compared with controls, and resulted in complete tumor rejection in 40% (2/5) of mice (FIG. 11A). In contrast, vaccination with pNeuTm or treatment with Leg-NP-CDDO alone did not protect against tumor recurrence. These results suggest that combination therapy-mediated protection against tumor recurrence results from Leg-NP-CDDO, which Th1-primes the immune TME thus improving anti-tumor immune responses following pNeuTm vaccination.

Splenocytes from pNeuTm vaccinated mice, combined with Leg-NP-CDDO, Leg-NP or PBS, were cultured with irradiated MMTV-Neu primary tumor cells and their CTL response measured by flow cytometry. Results showed that pNeuTM vaccinated mice treated with Leg-NP-CDDO had a 2.3-fold increase in the percentage of $CD8^+/Granzyme\ B^+$ splenocytes compared with controls (FIG. 11B). Additionally, to evaluate whether this boost in CTL responses was tumor cell specific, the CTL response of splenocytes from Leg-NP-CDDO/pNeuTm treated mice were compared when cultured with either HER-$2^{high}$ MMTV-Neu tumors cells versus HER-$2^{low}$ HEVc mouse endothelial cells (FIG. 11C). Flow cytometry analysis of these splenocytes revealed a 4-fold increase in percentage of $CD8^+/Granzyme\ B^+$ cells in response to HER-$2^{high}$ cells versus HER-$2^{low}$ cells (FIG. 11C), thus demonstrating that the immune response of mice treated with the combination therapy was indeed tumor antigen specific.

Discussion

Increased $CD8^+$ T cells in tumors of Leg-NP-CDDO treated mice correlated with marked increases in IL-15 expression, a potent chemoattractant for T cells. Importantly, IL-15 stimulates Th1 T cell differentiation and proliferation of naïve human and memory $CD8^+$ T cells in vitro. Significantly, these findings are consistent with the observation correlating increased IL-15 expression in the TME with improved $CD8^+$ T cell function as a result of STAT-3 inhibition with Leg-NP-CDDO.

Tumor-associated macrophages (TAMs) are among the most common immune cells in solid tumors. TAMs mediate pro-tumor inflammation by cytokine release prompting further recruitment of inflammatory cells (24). Concordantly, we found here a decrease in protein expressions of IL-10 and TGF-β in primary tumors, both reported to induce the cancer promoting M2 phenotype of TAMs. In contrast, macrophages that are activated by IFN-γ possess a phenotype associated with tumor destruction. These M1 macrophages are characterized in part by expression of NOS-2. Intriguingly, an increased infiltration of NOS-$2^+$ macrophages in primary tumors of mice treated with Leg-NP-CDDO which corresponded with an increased expression of GM-CSF in primary tumors was observed. Importantly, GM-CSF was shown to induce recruitment of enhanced professional antigen-presenting cells, including DCs and macrophages.

The present results demonstrate that targeted manipulation of the immune TME with Leg-NP-CDDO combined with a HER-2 DNA vaccine (pNeuTm) essentially prevented breast cancer recurrence in the mouse tumor model. Combination therapy also significantly improved anti-tumor CTL responses of $CD8^+$ T cells, when compared with mice receiving single therapy alone. Furthermore, mice treated with the combination therapy showed enhanced CTL responses specifically against primary tumor cells, but not HER-$2^-$ endothelial cells, thus demonstrating a tumor antigen specific immune response. Importantly, the combination therapy delayed tumor growth after re-challenging with HER-$2^+$ primary tumor cells and protected against recurrence in 40% of mice. These results clearly demonstrate that therapeutic manipulation of the immune TME can improve the efficacy of cancer immunotherapy.

Taken together, the results of described herein align with findings of several phase I/II clinical trials showing limited effects by single cytokine therapies, which strongly emphasized the need for combination therapies and specific targeting of multiple cytokines. Significantly, the findings herein represent a novel targeted therapeutic approach to manipulate a major repertoire of immune cytokines and growth factors in the TME. Importantly, by targeting immune manipulations for Th1/Th2 transitions specifically in the TME, serious systemic toxicities of many immune-stimulating cytokines may be circumvented, while utilizing their immune promoting effects. By improving the anti-tumor effects of cancer vaccine therapy and preventing cancer recurrence, Leg-NP-CDDO represents a potentially useful therapeutic compound that can ultimately improve the efficacy of cancer immunotherapy to increase lifespan and health of cancer patients.

In summary, a novel legumain-targeted PEG-liposome NP capable of highly efficient drug payload delivery to solid tumors in vivo has been developed. Coupling to RR-11a significantly enhanced NP uptake by tumor cells under hypoxic stress, a hallmark of solid tumors, due to a marked increase in the number of legumain binding sites on the surface of tumor cells. This phenomenon, in conjunction with the high binding affinity of RR-11a for legumain, facilitates the specific homing of drug loaded RR-11a$^+$ NPs to solid tumors in a therapeutic setting, reducing non-specific accumulation in the liver and heart, thus eliminating undesired drug toxicity. Importantly, drug delivery by RR-11a$^+$ NPs not only eliminated the toxicity of lethal doses of doxorubicin, but also increased the sensitivity of tumors to low doses of doxorubicin, thus reducing the amount of drug required to achieve an effective anti-tumor response.

activated CD8$^+$ T cells, M1 macrophages, and dendritic cells was observed. These changes correlated with delayed growth of orthotopic 4TO7 breast tumors and, when combined with a HER-2 DNA vaccine, prevented HER-2$^+$ primary tumor recurrence in immune competent mice. Furthermore, anti-tumor T cell responses were enhanced in splenocytes isolated from mice treated with this combination therapy. Together, these data demonstrate effective protection from cancer recurrence through improved immune surveillance against a tumor-specific antigen.

The tumor targeting NP's have significant clinical applications since the RR-11a$^+$ NPs used to encapsulate doxorubicin and CDDO-Im can also be applied to encapsulate other drug compounds, including drug combinations such as doxorubicin and taxanes, which would virtually eliminate differences in their pharmacokinetics. This technology advances the current state of drug delivery and chemotherapy, providing a means for reducing the biologically optimal drug dose required for an anti-tumor effect while at the same time eliminating undesired systemic toxicities, which could significantly improve health and quality of life of cancer patients.

EXAMPLE 7

Preparation of Additional Vesicle-Forming Lipid Materials and Legumain-Targeting Lipid Components

EXAMPLE 7A

Synthesis of (2S)-2-(((9H-fluoren-9-yl)methoxy) carbonylamino)-glutamic acid-α-tert-butylester-γ-2, 3-bis(tetradecyloxy)propyl-amide

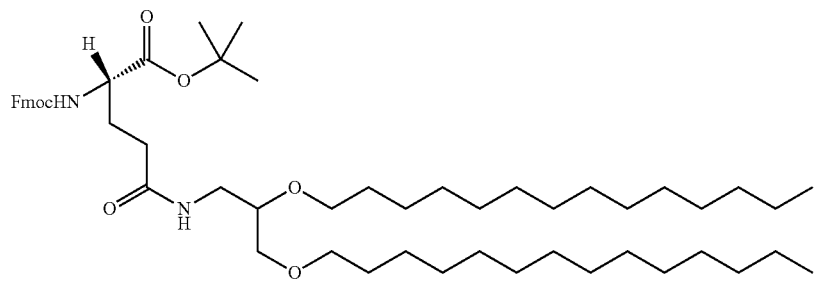

The tumor microenvironment (TME) mediates immune suppression resulting in tumor cell escape from immune surveillance and cancer vaccine failure. Immune suppression is mediated by the STAT-3 transcription factor, which potentiates signaling in tumor and immune cells. Since immune suppression continues to be a major inhibitor of cancer vaccine efficacy, we examined in this study whether therapeutically targeted delivery of a synthetic STAT-3 inhibitor to the TME, combined with a HER-2 DNA vaccine can improve immune surveillance against HER-2$^+$ breast cancer and prevent its recurrence. The ligand-targeted nanoparticle (NP) encapsulating a CDDO-Im payload is capable of specific delivery to the TME, which demonstrated an effective therapeutic inhibition of STAT-3 activation in primary tumors. Furthermore, treatment with these NPs resulted in priming of the immune TME, characterized by increased IFN-γ, pSTAT-1, GM-CSF, IL-2, IL-15 and IL-12b and reduced TGF-β, IL-6 and IL-10 protein expression. Additionally, significantly increased tumor infiltration by 15 g of Fmoc-Glu(OSu)OtBu ((2S)—N-(9-fluorenylmethyloxycarbonyl)-glutamic acid α-tert-butyl-ester γ-N-hydroxysuccinimide ester) are dissolved in dichloromethane at room temperature. After addition of 15.3 g of 2,3-bis(tetradecyloxy)propan-1-amine, the mixture is stirred for 17 hours and evaporated to dryness. The residue is dissolved in a minimum amount of dichloromethane and purified by column chromatography using SiO$_2$ as solid phase and methyl tert. butylether/hexane/7:3 as eluent. After evaporation of product fractions 25.5 g of (2S)-2-(((9H-fluoren-9-yl) methoxy)carbonylamino)-glutamic acid-α-tert-butylester-γ-2,3-bis(tetradecyloxy)propyl-amide are obtained as a colorless solid. $^1$H-NMR in CDCl$_3$ (TMS as internal standard), chemical shift in ppm: 7.76 (d, 2H, Fmoc), 7.61 (d, 2H, Fmoc), 7.25-7.43 (m, 4H, Fmoc), 6.13 (bs, NH, 1H), 5.60 (bs, NH, 1H), 4.39, 4.18-4.25 (d and m, 4H), 3.21-3.62 (m, 9H), 1.97-2.23 (m, 4H), 1.51-1.60 (m, 4H), 1.47 (s, 9H), 1.25 (m, 44H, CH$_2$), 0.84-0.91 (m, 6H, 2× alkyl-CH$_3$).

EXAMPLE 7B

Synthesis of (2S)-2-(((9H-fluoren-9-yl)methoxy)carbonylamino)-glutamic acid-γ-2,3-bis(tetradecyloxy)propyl-amide

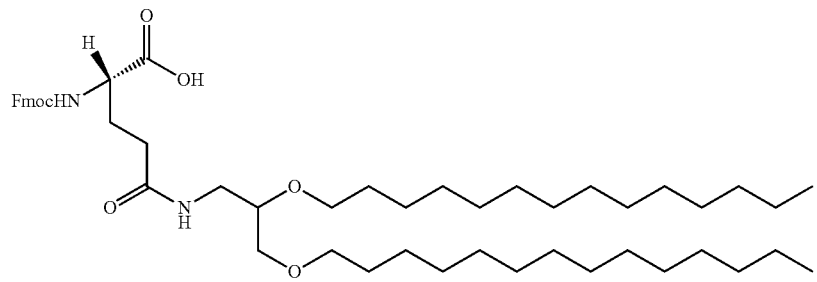

In a 100 mL flask 4.6 g (5.1 mmol) (2S)-2-(((9H-fluoren-9-yl)methoxy)carbonylamino)-glutamic acid-α-tert-butylester-γ-2,3-bis(tetradecyloxy)propyl-amide are dissolved in 25 mL dichloromethane and treated with 25 mL trifluoroacetic acid. After 1 h the ester group is completely cleaved and the solution is poured onto 50 mL of cold water. The organic layer is extracted, washed to neutral pH with water and dried over $Na_2SO_4$. The organic layer is filtered off and the solvent evaporated to afford 4.2 g of the desired product (5.0 mmol, 98% yield, TLC: MtBE/hexane 7:3; Rf=0.43).

EXAMPLE 7C

Synthesis of (2S)-glutamic acid-γ-(2,3-bis(tetradecyloxy)propyl)amide

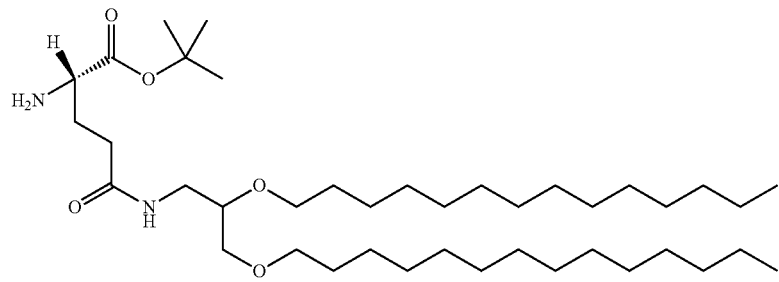 [SMILES: CCCCCCCCCCCCCCOCC(CNC(=O)CC[C@H](N)C(=O)OC(C)(C)C)OCCCCCCCCCCCCCC]

5 g of (2S)-2-(((9H-fluoren-9-yl)methoxy)carbonylamino)-glutamic acid-α-tert-butylester-γ-2,3-bis(tetradecyloxy)propyl-amide are added to 85 mL of N,N-dimethylformamide. To the mixture 2.6 mL of piperidine are added. The mixture is stirred for three hours at room temperature and then evaporated to dryness under vacuum to give 5.2 g of (2S)-glutamic acid-γ-(2,3-bis(tetradecyloxy)propyl)amide as a colorless solid, which can be used in the preparation of lipidic vesicles or for prior derivatization with an active agent or a spacer group (e.g., a PEG group and the like).

EXAMPLE 7D

Synthesis of (5S,8S,45S,E)-11-(2-amino-2-oxoethyl)-45-(3-((2,3-bis(tetradecyloxy)propyl)amino)-3-oxopropyl)-5,8-dimethyl-3,6,9,12,15,43-hexaoxo-1-phenyl-2,19,22,25,28,31,34,37,40-nonaoxa-4,7,10,11,16,44-hexaazahexatetracont-13-en-46-oic acid

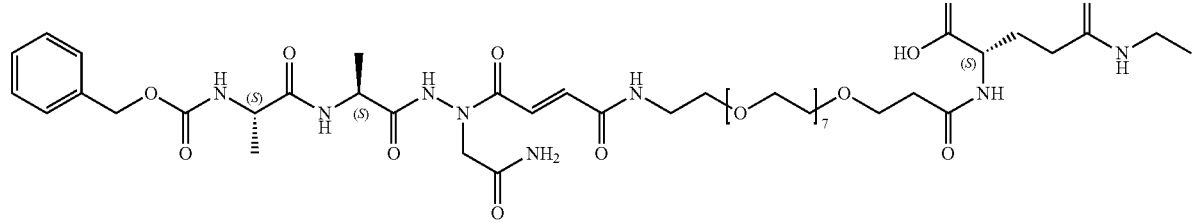

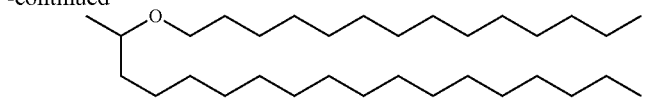

(a) Synthesis of Fmoc-Glu(DMA)-diphenylmethyl resin:

In a 100 mL solid phase peptide synthesis (SPPS) reactor 3.85 g of diphenyldiazomethane resin (3.3 mmol) are washed twice with 30 mL DCM and treated with a solution of 4.2 g of 2S)-2-(((9H-fluoren-9-yl)methoxy)carbonylamino)-glutamic acid-γ-2,3-bis(tetradecyloxy)propylamide (see Example 7A, 1.5 eq., 5.0 mmol) in 30 mL DCM overnight. The solution is filtered off and the resin is washed with DCM four times. To destroy eventually un-reacted diphenyldiazomethane the resin is treated with 125 µL acetic acid (0.5 eq., 2.2 mmol) in 30 mL DCM for 15 minutes and washed afterwards three times alternating with 30 mL dimethylformamide and isopropanol. The resin is washed twice with diisopropyl ether and dried overnight in vacuo. 6.7 g of the desired product are obtained (>100% of theory, yield in theory 6.5 g). The loading of the resin is determined to 0.49 mmol/g by UV measurement of the Fmoc cleavage product at 304 nm (maximum loading in theory 0.51 mmol/g).

(b) Synthesis of RR-11a-NH-PEG$_8$-PA-Glu(DMA)-diphenylmethyl resin:

RR-11a-NH-PEG$_8$-PA-Glu(DMA)-diphenylmethyl resin is obtained through conventional solid phase synthesis by the following reaction sequence:

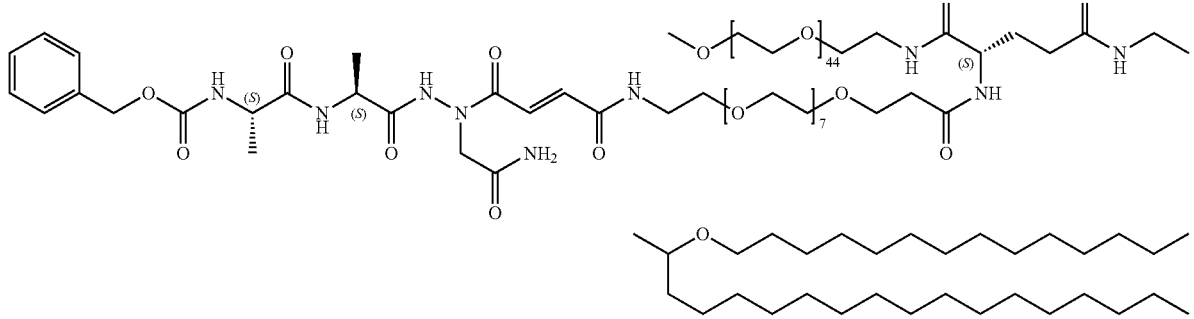

(1) cleavage of the Fmoc group of the Fmoc-Glu(DMA)-diphenylmethyl resin with piperidine in DMF,
(2) condensation with Fmoc-NH-PEG$_8$-PA using PyBOP in DMF and DIPEA,
(3) cleavage of the Fmoc group of the Fmoc-NH-PEG$_8$-PA-Glu(DMA)-diphenylmethyl resin with piperidine in DMF and finally,
(4) condensation with RR-11a-OH using PyBOP in DMF and DIPEA.

(c) Synthesis of (5S,8S,45S,E)-11-(2-amino-2-oxoethyl)-45-(3-((2,3-bis(tetradecyloxy)propyl)amino)-3-oxopropyl)-5,8-dimethyl-3,6,9,12,15,43-hexaoxo-1-phenyl-2,19,22,25,28,31,34,37,40-nonaoxa-4,7,10,11,16,44-hexaazahexatetracont-13-en-46-oic acid:

7.15 g RR-11a-NH-PEG$_8$-PA-Glu(DMA)-diphenylmethyl resin are washed with 50 mL dichloromethane each, filtered off, suspended again in 50 mL dichloromethane and dried in vacuo. Then 70 mL of a 5% solution of trifluoroacetic acid in dichloromethane were added. The suspension is stirred at room temperature for 3.5 hour and then filtered into 100 mL cold diisopropylether. The resin is rinsed with dichloromethane/diisopropylether (1/1). The combined filtrates are evaporated in vacuo and lyophilyzed from t-BuOH to yield 4.15 g (92%) of an amber solid. ESI-MS: monoisotopic $M_{W\ calc.}$=1481.9, $M_W$ [M−H]$^-$=1480.2.

EXAMPLE 7E

Synthesis of (5S,8S,45S,E)-11-(2-amino-2-oxoethyl)-45-(3-((2,3-bis(tetradecyloxy)propyl)amino)-3-oxopropyl)-5,8-dimethyl-3,6,9,12,15,43-hexaoxo-1-phenyl-2,19,22,25,28,31,34,37,40-nonaoxa-4,7,10,11,16,44-hexaazahexatetracont-13-en-46-oic acid 7.15 g RR-11a-NH-PEG$_8$-PA-Glu(DMA)-OH (product of Example 7D, step (c)) and 1.50 mL DIPEA are dissolved in 70 mL dichloromethane. Then 4.32 g MeO-PEG-NH$_2$ and 1.67 g PyBOP are added and the solution is stirred overnight. The brown solution is evaporated and the residue is purified twice by column chromatography over 300 g silica gel (Merck 60, 0.040-0.063 mm) using a mixture of ethyl acetate, methanol and triethylamine in a ratio of 16:3.1 resp. 17:2:1. The product containing fractions are combined and evaporated and the resulting viscous residue is lyophilized from t-BuOH to yield 4.5 g (60%) of an yellowish solid. MALDI-MS: monoisotopic $M_{W\ calc.}$=3476.2, $M_W$ [M+Na]$^+$=3500, $M_n$=3363.2, $M_W$=3384.5, PDI=1.01

EXAMPLE 7F

Synthesis of benzyl ((2S,5S,14S,E)-8-(2-amino-2-oxoethyl)-14-carbamoyl-5-methyl-3,6,9,12,17-pentaoxo-20-(tetradecyloxy)-22-oxa-4,7,8,13,18-pentaazahexatriacont-10-en-2-yl)carbamate

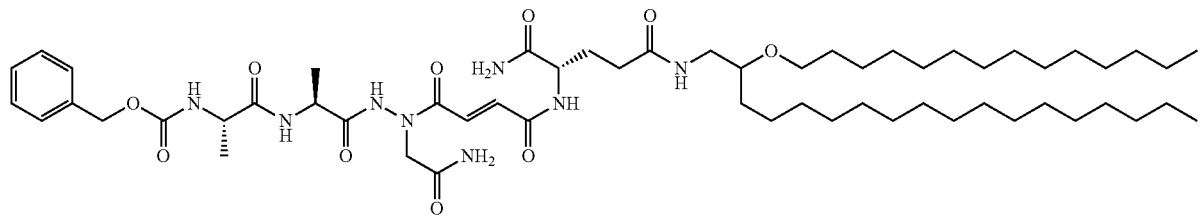 [SMILES: CCCCCCCCCCCCCCCCC(CNC(=O)CC[C@H](NC(=O)/C=C/C(=O)N(CC(N)=O)NC(=O)[C@H](C)NC(=O)[C@H](C)NC(=O)OCc1ccccc1)C(N)=O)OCCCCCCCCCCCCCC]

15

(a) Synthesis of Fmoc-Glu(DMA)-Sieber resin:

In a 100 mL SPPS reactor 5.0 g of Sieber resin (3.1 mmol) are washed twice with 50 mL DMF, treated with a 20% solution of piperidine in DMF over 15 min and washed three times alternatingly with 50 mL DMF and with 50 mL iPrOH. Then a solution of 3.2 g of (2S)-2-(((9H-fluoren-9-yl)methoxy)carbonylamino)-glutamic acid-γ-2,3-bis(tetradecyloxy)propyl-amide (1.25 eq., 3.8 mmol) and 2.48 g PyBOP (1.5 equ.) in 50 mL DMF, and 1.62 mL DIPEA (2.5 equ.) for 2.5 h. The solution is filtered off and the resin is washed three times alternatingly with 50 mL DMF and with 50 mL iPrOH.

(b) Synthesis of RR-11a-Glu(DMA)-Sieber resin:

RR-11a-Glu(DMA)-Sieber resin is obtained through conventional solid phase synthesis by the following reaction sequence:
 (1) cleavage of the Fmoc group of the Fmoc-Glu(DMA)-Sieber resin with piperidine in DMF (5.6 g resin after drying in vacuo).
 (2) condensation with RR-11a-NHS using DIPEA in DMF.

(c) Cleavage of the Product from the Resin:

2.6 g RR-11a-Glu(DMA)-Sieber resin are treated with 20 mL 5% trifluaroacetic acid in dichloromethane for 2 h. The suspension is filtered into 100 mL cold diisopropylether. The filtrate is evaporated in vacuo and lyophilyzed from t-BuOH to yield 660 mg of a yellowish solid. ESI-MS: monoisotopic $M_{W\ calc.}$=1056.7, $M_W [M-H]^-$=1056.0.

EXAMPLE 7G

Synthesis of benzyl ((2S,5S,42S,E)-8-(2-amino-2-oxoethyl)-42-carbamoyl-5-methyl-3,6,9,12,40,45-hexaoxo-48-(tetradecyloxy)-16,19,22,25,28,31,34,37,50-nonaoxa-4,7,8,13,41,46-hexaazatetrahexacont-10-en-2-yl)carbamate

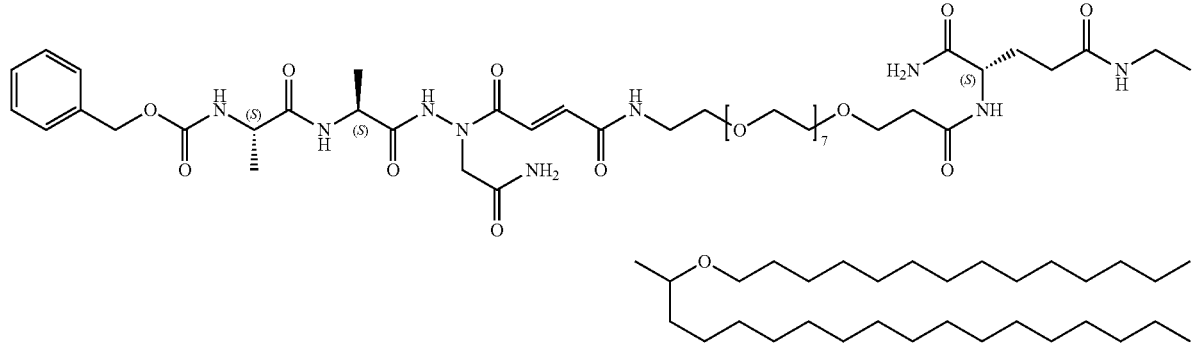

(a) Synthesis of Fmoc-Glu(DMA)-Sieber Resin: (see Example 7F).

(b) Synthesis of $NH_2$-$PEG_8$-PA-Glu(DMA)-Sieber resin: $NH_2$-$PEG_8$-PA-Glu(DMA)-Sieber resin is obtained through conventional solid phase synthesis by the following reaction sequence:
(1) cleavage of the Fmoc group of the Fmoc-Glu(DMA)-Sieber resin with piperidine in DMF,
(2) condensation with Fmoc-NH-$PEG_8$-PA using HBTU in DMF and DIPEA and finally
(3) cleavage of the Fmoc group of the Fmoc-NH-$PEG_8$-PA-Glu(DMA)-Sieber resin with piperidine in DMF.

(c) Synthesis of $NH_2$-$PEG_8$-PA-Glu(DMA)-amide:
The product is cleaved from the $NH_2$—$PEG_8$-PA-Glu(DMA)-Sieber resin using trifluoroacetic acid in dichloromethane. ESI-MS: monoisotopic $M_{W\ calc.}$=1034.8, $M_W$ $[M+H]^+$=1035.9.

(d) Synthesis of benzyl ((2S,5S,42S,E)-8-(2-amino-2-oxoethyl)-42-carbamoyl-5-methyl-3,6,9,12,40,45-hexaoxo-48-(tetradecyloxy)-16,19,22,25,28,31,34,37,50-nonaoxa-4,7,8,13,41,46-hexaazatetrahexacont-10-en-2-yl)carbamate:

A 5 mL round bottom flask equipped with mechanical stirrer is charged with 42 mg of $NH_2$-PEG8-PA-Glu(DMA)-amide (40.6 mmol) in 2 mL dichloromethane. Then 0.01 mL triethylamine (95 mmol) are added. A light yellow solution results after 2-3 minutes of stirring and 23 mg of RR-11a-NHS (41 mmol) are added over a period of 3 min. The solution is stirred for 1 hr and evaporated under reduced pressure resulting in an off-white solid product. The product shows a single spot in TLC. $M_{W\ calc.}$=1480.0, $M_W$ [M+H]$^+$=1482 and $M_W$ [M+Na]$^+$=1504.0.

EXAMPLE 7H

Synthesis of benzyl ((2S,5S,126S,E)-8-(2-amino-2-oxoethyl)-126-carbamoyl-5-methyl-3,6,9,12,124,129-hexaoxo-132-(tetradecyloxy)-16,19,22,25,28,31,34,37,40,43,46,49,52,55,58,61,64,67,70,73,76,79,82,85,88,91,94,97,100,103,106,109,112,115,118,121,134-heptatriacontaoxa-4,7,8,13,125,130-hexaazaoctatetracontahect-10-en-2-yl)carbamate

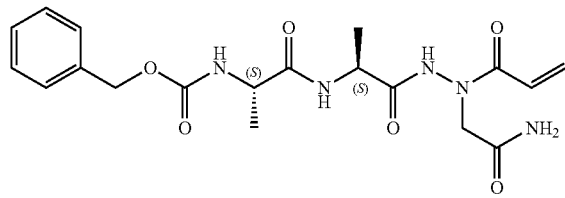

(a) Synthesis of Fmoc-Glu(DMA)-Sieber Resin: (see Example 7F, Step (a)).

(b) Synthesis of RR-11a-NH-$PEG_{36}$-PA-Glu(DMA)-Sieber resin:
RR-11a-NH-$PEG_{36}$-PA-Glu(DMA)-Sieber resin is obtained through conventional solid phase synthesis by the following reaction sequence:
(1) cleavage of the Fmoc group of the Fmoc-Glu(DMA)-Sieber resin with piperidine in DMF,
(2) condensation with Fmoc-NH-$PEG_{36}$-PA using PyBOP in DMF and DIPEA,
(3) cleavage of the Fmoc group of the Fmoc-NH-$PEG_{36}$-PA-Glu(DMA)-Sieber resin with piperidine in DMF and finally,
(4) condensation with RR-11a-NHS using DIPEA in DMF.

(c) Synthesis of benzyl ((2S,5S,126S,E)-8-(2-amino-2-oxoethyl)-126-carbamoyl-5-methyl-3,6,9,12,124,129-hexaoxo-132-(tetradecyloxy)-16,19,22,25,28,31,34,37,40,43,46,49,52,55,58,61,64,67,70,73,76,79,82,85,88,91,94,97,100,103,106,109,112,115,118,121,134-heptatriacontaoxa-4,7,8,13,125,130-hexaazaoctatetracontahect-10-en-2-yl) carbamate:

7.0 g RR-11a-NH-$PEG_{36}$-PA-Glu(DMA)-Sieber resin are treated with 70 mL of a 2% solution of trifluaroacetic acid in dichloromethane are added. The suspension is stirred at room temperature for 3 h and then filtered into 70 mL cold diisopropylether. The filtrate is evaporated in vacuo and lyophilyzed from t-BuOH to yield 1.25 g of a white solid. ESI-MS: monoisotopic $M_{W\ calc.}$=2713.7, $M_W$ [M+Na+H]$^{2+}$=1380.1.

We claim:
1. An aqueous tumor-targeting liposome nanoparticle composition comprising an aqueous dispersion of liposome nanoparticles; the liposome nanoparticles comprising a legumain-targeting lipid component and a polyethylene glycol-conjugated lipid component; the legumain-targeting lipid component comprising a hydrophobic lipid portion covalently attached to a legumain-binding moiety, wherein the legumain-targeting lipid component comprises a compound of the Formula:

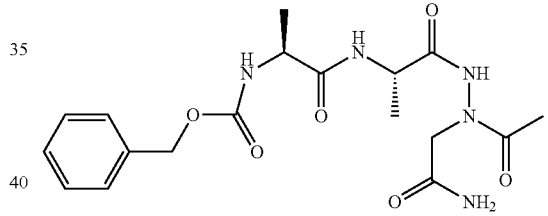

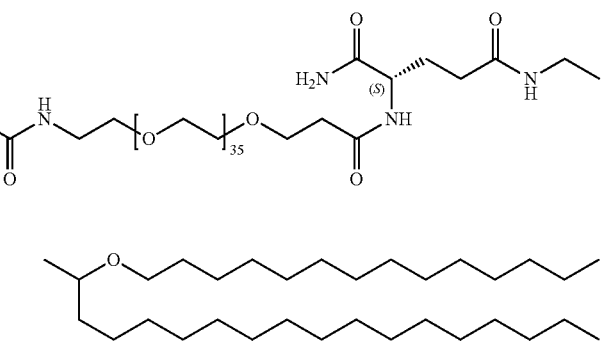

-continued

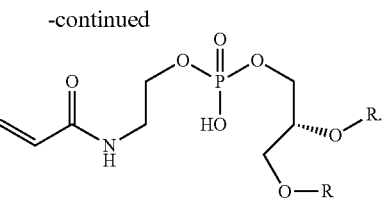

—R =

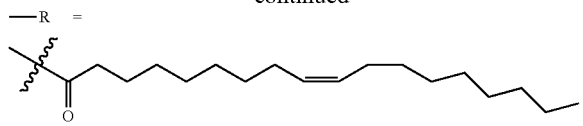

2. The composition of claim 1, wherein the hydrophobic lipid portion of the legumain-targeting lipid component comprises a 1,2-diacylglycero-phosphoalkanolamine group.

3. The composition of claim 2, wherein the 1,2-diacyl-glycero-phosphoalkanolamine is 1,2-dioleoyl-sn-glycerol-3-phosphoethanolamine (DOPE).

4. The composition of claim 1, wherein the polyethylene glycol-conjugated lipid component comprises a polyethylene glycol-conjugated 1,2-diacylglycero-phosphoalkanolamine compound.

5. The composition of claim 4, wherein the polyethylene glycol-conjugated 1,2-diacylglycero-phosphoalkanolamine compound comprises 1,2-dioleoyl-sn-glycerol-3-phosphoethanolamine-N-[methoxy(polyethylene glycol] wherein the polyethylene glycol portion of the compound has an average molecular weight of about 2000 atomic mass units (amu).

6. The composition of claim 1, further comprising one or more of a zwitterionic lipid component; an amino-substituted lipid component; and a neutral lipid component.

7. The composition of claim 6, wherein the zwitterionic lipid component comprises a 1,2-diacylglycero-phosphocholine compound.

8. The composition of claim 7, wherein the 1,2-diacyl-glycero-phosphocholine compound comprises 1,2-di-(9Z-octadecenoyl)-sn-glycero-3-phosphocholine (DOPC).

9. The composition of claim 6, wherein the amino-substituted lipid component comprises a 1,2-diacylglycero-phosphoalkanolamine compound.

10. The composition of claim 9, wherein the 1,2-diacyl-glycero-phosphoalkanolamine compound comprises DOPE.

11. The composition of claim 6, wherein the neutral lipid component comprises cholesterol.

12. The composition of claim 6, wherein the liposome nanoparticles encapsulate an anti-cancer chemotherapeutic agent.

13. The composition of claim 12, wherein the anti-cancer chemotherapeutic agent comprises doxorubicin or 1-[2-cyano-3,12-dioxooleana-1,9(11)-dien-28-oyl]imidazole (CDDO-Im).

14. The composition of claim 13 wherein the anti-cancer chemotherapeutic agent is doxorubicin.

15. The composition of claim 12, wherein the anti-cancer chemotherapeutic agent comprises at least one compound selected from the group consisting of cisplatin; carboplatin; oxaliplatin; mechlorethamine; cyclophosphamide; chlorambucil; ifosfamide; 5-fluorouricil; floxuridine; cytosine arabinoside; mercaptopurine; thioguanine; azathioprine; fludarabine; pentostatin; cladribine; etoposide; etoposide phosphate; teniposide; amsacrine; paclitaxel; methotrexate; trimethoprim; pyrimethamine; pemetrexed; vitaxin; anecorvate; angiostatin; endostatin; squalamine; an antiangiogenic tryptophanyl-t-RNA sythetase peptide fragment; bevacizumab; tivozanib; vandetanib; vatalanib; alemtuzumab; cetuximab; gemtuzumab; ibritumomab; pantitumumab; rituximab; tositumomab; trastuzumab; actinomycin; bleomycin; plicamycin; mitomycin; doxorubicin; epirubicin; daunorubicin; valrubicin; idarubicin; ursolic acid; a 2-cyano-3,12-dioxooleana-1,9-dien-28-oic ester, a 2-cyano-3,12-dioxooleana-1,9-dien-28-oic amide; 1-[2-cyano-3,12-dioxooleana-1,9(11)-dien-28-oyl]imidazole (also known as CDDO-Im); as well as physiologically acceptable salts and prodrugs thereof.

16. The composition of claim 1, wherein the liposome nanoparticles encapsulate an anti-tumor agent.

17. The composition of claim 16, wherein the anti-tumor agent is an agonist or antagonist of a receptor or a receptor ligand involved in tumor growth.

* * * * *

UNITED STATES PATENT AND TRADEMARK OFFICE
CERTIFICATE OF CORRECTION

PATENT NO. : 10,335,420 B2
APPLICATION NO. : 15/495474
DATED : July 2, 2019
INVENTOR(S) : Ralph A. Reisfeld et al.

Page 1 of 1

It is certified that error appears in the above-identified patent and that said Letters Patent is hereby corrected as shown below:

In the Specification

Column 4,
Line 53, "(long/mL)" should be -- (10ng/mL) --.

Column 10,
Line 4, "NETS-ester" should be -- NHS-ester --.

Column 25,
Line 13, "4.2 g of 25" should be -- 4.2 g of 2S --.

Column 26,
Lines 2-5 and 48-51, the chemical structure, each occurrence, should be depicted as follows:

Column 28,
Lines 8-11 and 63-66, the chemical structure, each occurrence, should be depicted as follows:

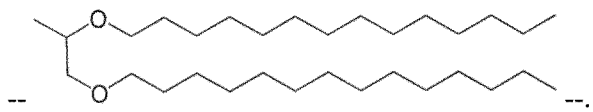

Column 30,
Lines 53-56, the chemical structure should be depicted as follows:

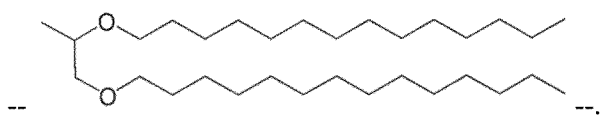

Signed and Sealed this
Twenty-second Day of October, 2019

Andrei Iancu
*Director of the United States Patent and Trademark Office*